(12) United States Patent
Steinmetzer et al.

(10) Patent No.: US 7,407,982 B2
(45) Date of Patent: Aug. 5, 2008

(54) OLIGO OR POLYALKYLENE GLYCOL-COUPLED THROMBIN INHIBITORS

(75) Inventors: Torsten Steinmetzer, Jena (DE); Götz Nowak, Erfurt (DE)

(73) Assignee: HaemoSys GmbH, Jena (DE)

( * ) Notice: Subject to any disclaimer, the term of this patent is extended or adjusted under 35 U.S.C. 154(b) by 482 days.

(21) Appl. No.: 10/344,722

(22) PCT Filed: Jan. 23, 2002

(86) PCT No.: PCT/EP02/00652

§ 371 (c)(1),
(2), (4) Date: Dec. 10, 2003

(87) PCT Pub. No.: WO02/059065

PCT Pub. Date: Aug. 1, 2002

(65) Prior Publication Data

US 2005/0070479 A1    Mar. 31, 2005

(30) Foreign Application Priority Data

Jan. 23, 2001   (DE) ................ 101 02 878

(51) Int. Cl.
  *A61K 31/40*   (2006.01)
  *C07D 209/54*   (2006.01)
(52) U.S. Cl. .................. 514/408; 548/408
(58) Field of Classification Search ........ 514/408; 548/400
See application file for complete search history.

(56) References Cited

U.S. PATENT DOCUMENTS 5,583,146 A    12/1996   Kimball et al. .......... 514/326
5,798,377 A *  8/1998   Lumma et al. ........... 514/423
5,914,319 A *  6/1999   Schacht et al. .......... 514/19

FOREIGN PATENT DOCUMENTS

EP    0658585    11/1994
WO    WO91/08229   6/1991
WO    WO98/32466   7/1998

OTHER PUBLICATIONS

Zalipsky S., "Chemistry of polyethylene glycol conjugates with biologically active molecules," Advanced Drug Delivery Reviews, 16 (1995) pp. 157-182.
Lorand, L., et al., "a double-headed Gly-Pro-Arg-Pro Ligand mimics the functions of the E domain of fibrin for promoting the end-to-end crosslinking of γ chains by factor XIII$_a$," Proceedings of the National Academy of Sciences of the United States, Jan. 1998, vol. 95, pp. 537-541.
Steinmetzer, T., et al., "New Thrombin Inhibitors Based on D-Cha-Pro-Derivatives," Journal of Enzyme Inhibition, vol. 14, 1999, pp. 203-216.
Poschel, K., et al., "Parmacodynamics and pharmacokinetics of polyethylene glycol-hirudin in patients with chronic renal failure," Kidney International, vol. 58, 2000, pp. 2478-2484.
Boyer, J.R., et al., "Solubilisation of Ferricytachrome C in Methanol Using a Crown Ether Absorption, Circular Dichroism and EPR Spectral Properties," Biochemical and Biophysical Research Communications, vol. 127, No. 3, 1985, pp. 828-835.

* cited by examiner

*Primary Examiner*—Golam M. M. Shameem
*Assistant Examiner*—Susannah Chung
(74) *Attorney, Agent, or Firm*—Kagan Binder, PLLC

(57) ABSTRACT

The present invention relates to novel covalent oligo and polyalkylene glycol conjugates with synthetic inhibitors of trypsin-type serine proteases, in particular inhibitors of the hemocoagulation protease thrombin, synthetic intermediates stages required in their production and their use for producing active ingredients for the treatment or prophylaxis of thrombotic complications.

5 Claims, 9 Drawing Sheets

OLIGO OR POLYALKYLENE GLYCOL-COUPLED THROMBIN INHIBITORS

The present invention relates to novel covalent oligo and polyalkylene glycol conjugates with synthetic inhibitors of trypsin-type serine proteases, in particular inhibitors of the hemocoagulation protease thrombin, synthetic intermediate stages required in their production and their use for producing active ingredients for the treatment or prophylaxis of thrombotic complications.

The trypsin-type serine protease thrombin is the central enzyme in the hemocoagulation cascade. It inter alia cleaves fibrinogen, which results in a fibrin clot that is stabilized by subsequent cross-linkage catalyzed by the factor XIII a (Davie et al., 1991, *Biochemistry* 30, 10363-10370). The factor XIIIa itself is activated from its zymogen form by the catalytic activity of thrombin as well. Thrombin can additionally accelerate the hemocoagulation cascade by activating the factors V and VIII. Also, thrombin is capable of specifically stimulating the thrombin receptor on the thrombocyte surface, which leads to an activation of the platelets. Too high a thrombin activity can lead to different thrombotic complications such as e.g. a myocardial infarct, deep venous thrombosis, peripheral occlusive arterial diseases or pulmonary embolism. Thrombotic complications can also occur during treatments where blood comes in contact with non-physiological surfaces such as e.g. during surgical procedures, hemodialysis or in heart-lung machines.

By using the thrombin inhibitor hirudin, it was possible to verify that specific thrombin inhibitors have anticoagulant properties and are suitable for preventing thrombotic complications (Markwardt, 1970 *Methods in Enzymol.* 19, 924-932). Hirudin is a naturally occurring protein which has been isolated from the medical leech and has been available for several years in recombinant form. In the meantime, recombinantly produced hirudin has been approved for some indications, such as e.g. for the prevention of thromboses after hip joint surgery or heparin-induced thrombocytopenia (Menear, 1999 *Expert Opinion on Investigational Drugs* 8, 1373-1384).

Since recombinant proteins are expensive to produce, can only be administered parenterally and since exogenous proteins have an antigenic effect, intense research has been done to develop low-molecular synthetic thrombin inhibitors for use as orally effective anticoagulants. So far, despite concentrated efforts, only two low-molecular thrombin inhibitors, Argatroban and Gabexate Mesilate, have been approved in Japan, but these compounds as well are only effective parenterally and only remain in the bloodstream for a very short time. In 2000, Argatroban was approved in the U.S. as well.

It is known from literature that the retention time of proteins, inhibitors and other active ingredients in the bloodstream can be extended by means of covalent conjugation with macromolecules, such as e.g. polysaccharides or polyethylene glycols (PEG). This also applies e.g. to PEG-coupled hirudin (Kurfürst et al., WO 91/08229) or a PEG-coupled low-molecular thrombin inhibitor substance based on the CRC-220 (Stüber et al. *Peptide Research* 8, 78-85 (1995); Stüber and Koschinsky EP-A2-0 658 585). Both PEG-inhibitors show a longer half-life in the bloodstream of laboratory animals compared to the free unmodified compounds.

From the development of low-molecular thrombin inhibitors it is known that the basic amino acids arginine and lysine necessary for the bond, as well as their mimetics 4-amidinophenyl glycine or 3- and 4-amidinophenyl alanine, can be replaced with suitable decarboxylated analogues without any loss of thrombin affinity. Examples thereof include compounds with C-terminal agmatine (D-Phe-Pro-Agmatine; Bajusz et al., 1982 *Folia Haematol., Leipzig* 109, 16-21), noragmatine (Inogatran; Teger-Nilsson, WO 93/11152), 4-amidinobenzylamine (Melagatran, Antonsson et al., WO 94/29336 or Böhm et al., U.S. Pat. No. 5,852,051) or 4-amino-methyl-N-(amidino)-piperidine (Sanderson et al., 1997 *Bioorganic & Medicinal Chemistry Letters* 7, 1497-1500).

A problem that frequently occurs in the application of thrombin inhibitors is that the liver rapidly resorbs, metabolizes and secretes these substances. This can lead to the formation of new metabolites with undesired side-effects, some of which are released back into the blood circulation and are therefore only suitable with some reservations e.g. for the development of a drug. Resorption by the liver has been shown e.g. for thrombin inhibitors from completely different classes of substances such as e.g. CRC-220, TAPAP, NAPAP, Argatroban or Efegatran.

Surprisingly, we found that the oligo or polyalkylene glycol-bonded inhibitors (inhibitor conjugates) are increasingly, indeed almost completely, eliminated via the kidneys. This means that the covalent coupling of an oligo or polyalkylene glycol portion to the low-molecular synthetic thrombin inhibitors used by us modifies their manner of elimination. At the same time, the retention time of the inhibitor conjugates in the bloodstream is increased compared to the free inhibitors and so is their anticoagulant effect, which strictly depends on the concentration in the bloodstream (Hauptmann and Stürzebecher, 1999 *Thrombosis Research* 93, 203-241).

The term "inhibitor" as used in the present application refers to molecules that specifically bind to the active enter of the target enzyme and thus lead to its inhibition. If such molecules are integrated into the inhibitor conjugates of the present invention together with oligo or polyalkylene glycols, they form the inhibitor structure, i.e. the portion of the inventive conjugates whose structure allows a specific interaction with the target enzyme. Bivalent inhibitor conjugates indicate those whose oligo or polyalkylene portion is linked to two inhibitor structures.

We have found that by incorporating decarboxylated basic P1 groups in oligo and polyalkylene glycol-coupled compounds, highly potent thrombin inhibitor conjugates can be obtained. We have also found that thrombin inhibitors comprising substituted arginyl ketone derivatives as P1 groups can also be modified with oligo and polyalkylene glycols. When using such compounds, one does not have to depend on the expensive D-4-amidinophenyl-analine used in the PEG-coupled CRC-200 known from the prior art, nor on recombinant hirudin which is difficult to produce.

In contrast to free inhibitors, these oligo and polyalkylene glycol-coupled inhibitors are not, or only to a small extent, resorbed by the liver cells and metabolized there or transferred to the gall, but rather they are eliminated almost entirely via the kidneys. After subcutaneous application of the oligo and polyalkylene glycol-coupled inhibitors, prolonged inhibitor blood levels necessary for anticoagulation were determined, and it was found that the highly delayed transfer rate of the substances between the extravascular and the intravascular compartment was responsible for this effect. The uniform distribution after resorption from a subcutaneous injection deposit leads to an exclusive filling of the extracellular water compartment since the coupling of the inhibitors with oligo or polyalkylene glycols results in substances with enlarged hydration sheaths.

The compounds we developed have the general structure (I)

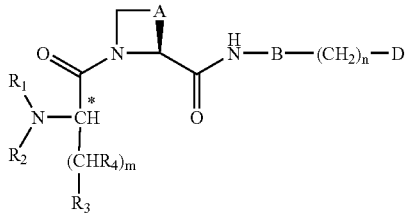

wherein
A is either a methylene, ethylene or propylene group and the ring formed therewith can be unsubstituted or substituted with a hydroxyl group, which is optionally etherified with an alkyl or aralkyl,
or one of the groups —$CH_2$—O—, —$CH_2$—S—, —$CH_2$—SO—, —$CH_2$—O—$CH_2$—, —$CH_2$—S—$CH_2$—, —$CH_2$—SO—$CH_2$—;
B is a bond or

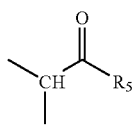

wherein $R_5$ is alkyl comprising 1 to 4, preferably 1 or 2 and especially preferred one carbon atom, and can be substituted with one or more identical or different halogen atoms, preferably Cl or F, or with a group

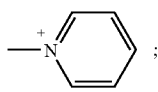

n is 0, 1, 2, 3, 4 or 5,
D represents a group

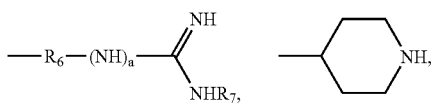

-continued

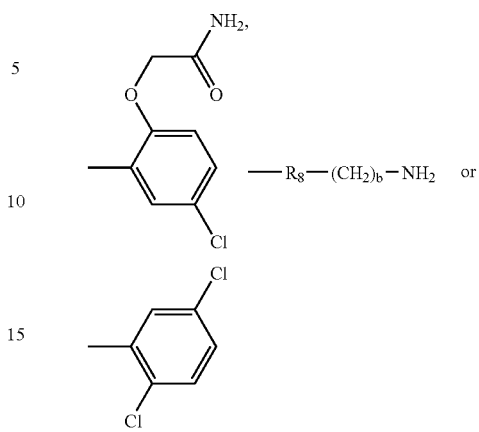

wherein and $R_6$ and $R_8$ are independently bivalent groups selected from aromatic or saturated 6-membered rings which can comprise a heteroatom, preferably a nitrogen atom, in addition to carbon and can carry one or more identical or different alkyl substituents, and wherein $R_6$ can furthermore be —NH— if a is 0, and $R_7$ is a hydrogen atom or —$NH_2$, and a is 0 or 1 and b is 0, 1 or 2;

$R_1$ is a hydrogen atom or arylsulfonyl, aralkylsulfonyl, cycloalkylmethylsulfonyl, cyclo-alkylethylsulfonyl or alkylsulfonyl group, the aryl portion of which can optionally carry one, two, three, four or five substituents independently selected from halogen atoms, alkyl or alkoxy groups or is linked with another aryl, and either
$R_2$ is —$(CH_2)_p$—CO—NH—$(CH_2)_q$—X, —$(CH_2)_r$—NH—CO—$(CH_2)_s$—V—X or —$(CH_2)_r$—NH—CO—O—$(CH_2)_s$—V—X wherein
p is an integer from 1 to 5 and q is an integer from 2 to 5;
r is an integer from 2 to 5 and s is an integer from 1 to 5;
V is a bond or —CO—NH—$(CH_2)_c$— and c is an integer from 2 to 5; and
X is an oligo or polyalkylene glycol with the structure —[O—$(CH_2)_d]_e$—OZ or —[O—CH($CH_3$)—$CH_2]_e$—OZ or a cycle with the structure

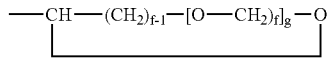

and d is an integer from 2 to 6, e is an integer from 3 to 1,000, Z is a hydrogen atom or alkyl or replicates the entire inhibitor structure bonded to the free valence of the group X, f is an integer from 2 to 6 and g is an integer from 3 to 10, preferably 3 to 7; and
$R_3$ is a phenyl or cyclohexyl group which can be substituted with 1 to 5 identical or different substituents independently selected from halogen atoms, alkyl, alkoxy or hydroxyl groups and $R_4$ is a hydrogen atom, phenyl or cyclohexyl group which can be substituted with 1 to 5 identical or different substituents independently selected from halogen atoms, alkyl, alkoxy or hydroxyl groups, with the hydrogen atom being preferred if m>1, m is 0, 1, 2, 3 or 4 and a D-configuration is present at the carbon atom marked with *;

or $R_2$ is a hydrogen atom and $R_3$ is —CO—NH—$(CH_2)_q$—X, —CO—$W_1$—$W_2$—$(CH_2)_q$—X, —NH—CO—$(CH_2)_s$—V—X, —NH—CO—O—$(CH_2)_s$—V—X, —S—$CH_2$—CO—NH—$(CH_2)_t$—X or —S—S—$CH_2$—$CH_2$—X, wherein q, s, X and V are as defined above and t is an integer from 2 to 5, and the group $W_1$ is —O— or —NH— and $W_2$ represents a bond or has the structure —$(CH_2)_v$—Ph—$(CH_2)_{v'}$-amide-, wherein v and v' are independently 0, 1 or 2, Ph represents a 1,2-, 1,3- or 1,4-substituted phenyl and amide represents —HN—(O)C— or —C(O)NH—, $R_4$ is a hydrogen atom, m is 1, 2, 3, 4 or 5 and an L-configuration is present at the carbon atom marked with *.

If the ring structure comprising A carries a substituent, it is preferably in the 4-position in the case of a 5-membered ring; in the case of a 6-membered ring, it is preferably in the 4- or 5-position. 5-membered rings whose ring structure comprises a second heteroatom introduced via the group A preferably carry this heteroatom in the 4-position. If A, together with its valencies, forms a 4-membered ring, it is preferably unsubstituted.

In formula (I), B preferably represents a bond or one of the following structures:

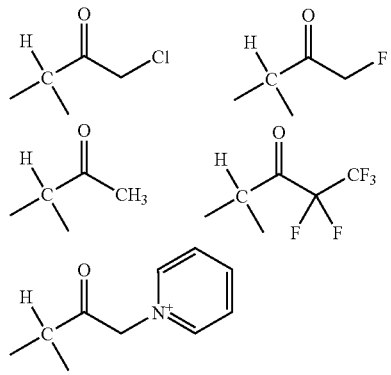

In group D of the general formula (I), $R_6$ is preferably 1,4-piperidinediyl, 1,3-piperidinediyl, 1,4-phenylene, 1,3-phenylene, 1,4-cyclohexanediyl, 1,3-cyclohexanediyl or —NH—. $R_8$ is preferably 1,4-phenylene, 1,3-phenylene, 1,4-cyclohexanediyl, 1,3-cyclohexanediyl or 2,5-pyridinediyl.

The following structures are especially preferred for D; with the bond marked with ~ they are linked to the rest of the general structure (I).

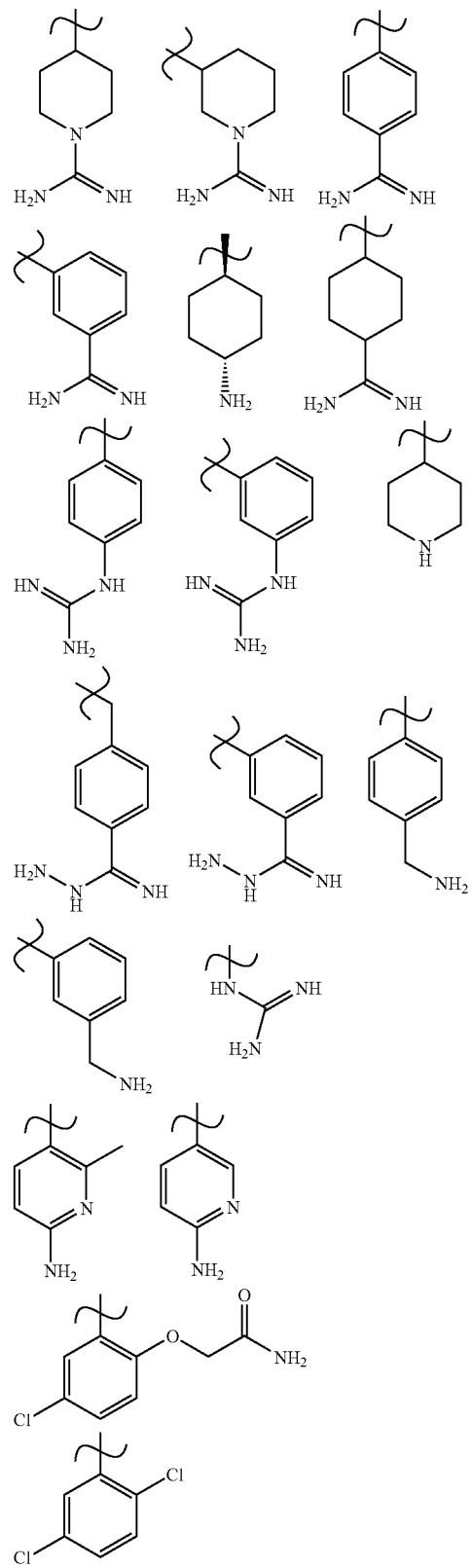

Preferred substituents of the aryl portion of $R_1$ are methyl, ethyl, propyl, methoxy or ethoxy groups. Cl, Br or F are preferably used as halogen atoms. Thus, preferred groups $R_1$ are for example 3-methoxy-phenylsulfonyl, 3,4-dichloro-phenylsulfonyl, benzylsulfonyl, 3,4-dimethoxy-phenylsulfonyl, 2,4,5-trichloro-phenylsulfonyl, 2-naphthyl-sulfonyl, 4-chloro-phenylsulfonyl, pentamethyl-phenylsulfonyl, 2,4,6-triisopropyl-phenylsulfonyl. An especially preferred $R_1$ is a 4-methoxy-substituted phenylsulfonyl group or a 4-methoxy-substituted phenylsulfonyl group additionally substituted with a chlorine atom or a methyl group in the 3-position. It can optionally also carry further methyl groups at the positions 2 and/or 6.

The oligo or polyalkylene portion of the compounds according to the invention comprised in X is preferably represented by a polyethylene glycol or polypropylene glycol, i.e. the parameters d and f are preferably 2 or 3. Preferred chain lengths can be inferred from the values of 3 and 500 of the parameter e; it is especially preferred that the resulting polyalkylene glycol have an average molecular weight between 750 and 20,000 Da, in particular around 750, 2,000, 3,000, 3,400, 5,000, 6,000, 10,1000 or 20,000 Da. If X forms a cyclic structure, i.e. a crown ether with the structure

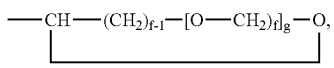

f is also preferably 2 and 3. Especially preferred values for g are 3, 4, 5 or 6 in this case.

It was surprisingly found that the effect of such crown ethers corresponds to that of polyalkylene glycol chains with a much higher molecular weight. For instance, crown ether conjugates made up of 5 PEG units exhibit elimination kinetics in the blood of rats that corresponds to that of polyethylene glycol (PEG) conjugates with a molecular weight of the PEG portion of 5,000 to 10,000 Da. Moreover, compared to linear polyalkylene glycols, which necessarily show a certain width in their molecular weight distribution, crown ethers are compounds of a uniform chemical definition, which is especially advantageous in the preparation of drugs.

If X has the structure —[O—$(CH_2)_d$]$_e$—OZ or —[O—CH$(CH_3)$—$CH_2$]$_e$—OZ and if Z is selected such that it corresponds to the inhibitor structure to which the group X is bonded with its free valence located at the end of the oligo or polyalkylene glycol structure directly opposite Z, a double inhibitor-functionalized oligo or polyalkylene glycol is formed. By means of such bifunctional conjugates, the inhibiting effect based on the number of molecules of structure (I) that are present can be increased. This can be advantageous, inter alia, in the modification of surfaces with molecules of the structure (I) if the goal is to achieve as high an inhibitor density per surface unit as possible.

Unless defined otherwise, the term "alkyl" as used in the present invention refers to linear or branched $C_1$-$C_8$ alkyl groups, preferably $C_1$-$C_5$, especially preferred $C_1$-$C_3$. Cycloalkyl groups comprise 3 to 8, preferably 3 to 6, carbon atoms. The term "alkoxy" relates to groups whose carbon chain comprises 1 to 8, preferably 1 to 5 and especially preferred 1 to 3 carbon atoms. The term "aralkyl" describes structures with 7 to 19, preferably 7 to 13, and especially preferred 7 to 9 carbon atoms. Aryl groups are groups with 6 to 18, preferably 6 to 12 and especially preferred 6 carbon atoms. This definition applies independently to every instance the above terms occur.

The following compounds of formulas (Ia-Ih) are especially preferred in the present invention:

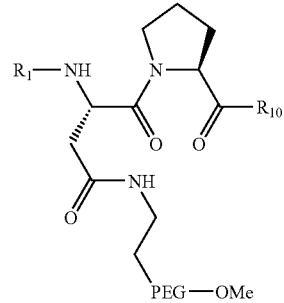
(Ia)

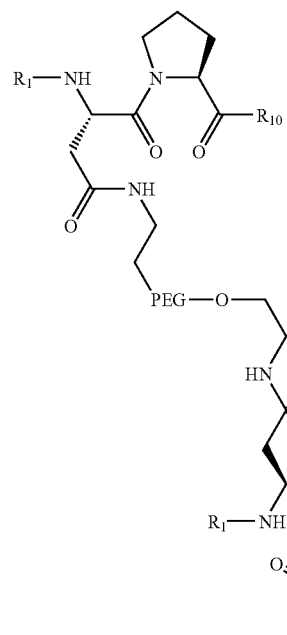
(Ib)

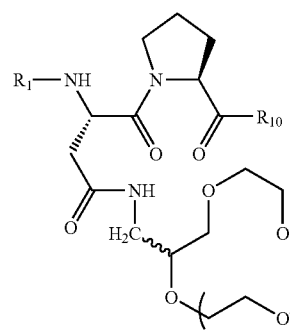
(Ic)

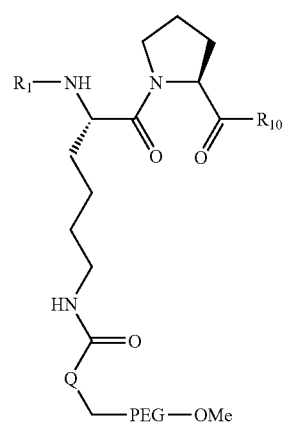
(Id)

-continued (Ie)

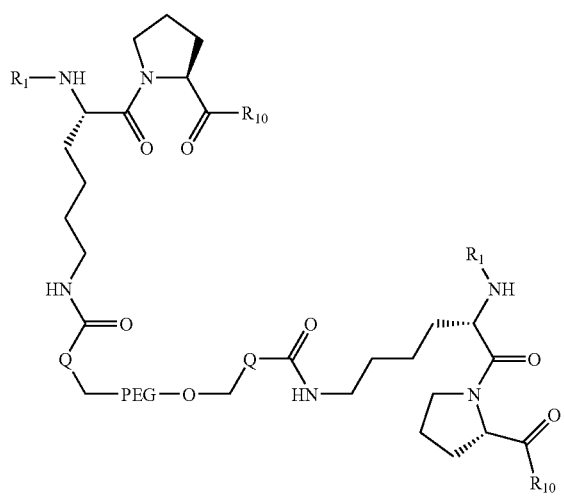

(If)

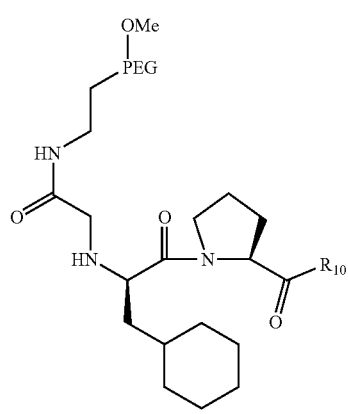

(Ig)

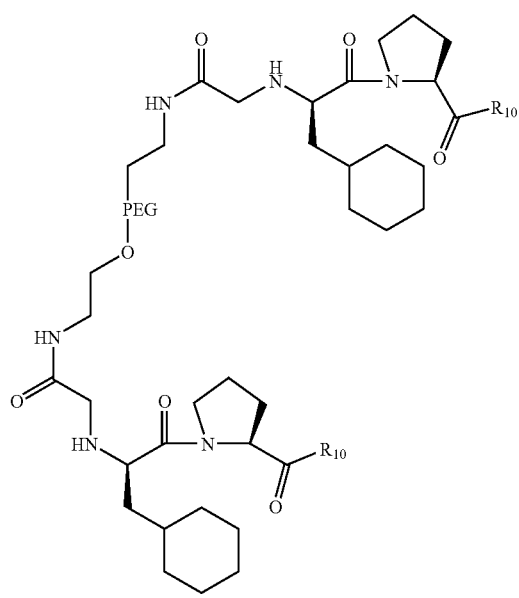

-continued (Ih)

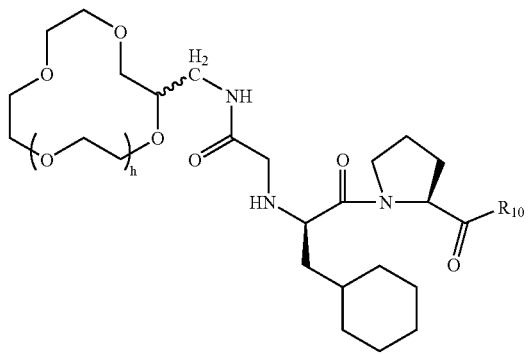

wherein $R_1$ is a 4-methoxy-phenylsulfonyl, 4-methoxy-3-chloro-phenylsulfonyl, 4-methoxy-3-methyl-phenylsulfonyl or 4-methoxy-2,3,6-trimethyl-phenylsulfonyl (Mtr) group, Q is —$(CH_2)_{s'}$—, wherein s'=0, 1, 2, 3 or 4, —O—$CH_2$— or —$CH_2$—$CH_2$—CO—NH—$CH_2$, and PEG is a polyethylene glycol structure of the formula -[O—$C_2H_4$]$_i$-, wherein i is 3 to 1,000, preferably 3 to 500, wherein values for i are preferred that result in an average molecular weight of the PEG of about 750 to 20,000 Da, preferably about 750, 2,000, 3,000, 3,400, 5,000, 6,000, 10,000 or 20,000. The variable h represents 1, 2, 3 or 4 and $R_{10}$ is

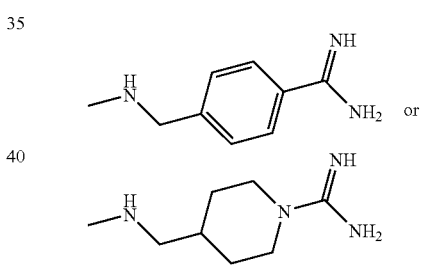

The compounds of the general formula (I) are prepared in a pharmaceutically suitable non-toxic salt form, e.g. as hydrochloride, hydrobromide, acetate, lactate, citrate, tosylate or trifluoroacetate salt. They can be used in solid or liquid form in common galenic types of application, e.g. as solutions, sprays, ointments or creams. They are prepared by means of common methods. The active ingredients can be formulated with the usual galenic additives such as fillers, preservatives, flow regulation agents, wetting agents, dispersing agents, emulsifiers, solvents and/or propellants (cf. H. Sucker et al., *Pharmazeutische Technologie* [Pharmaceutical Technology], Thieme publishing house, Stuttgart, 1978).

The compounds can be administered in a common manner orally or parenterally (subcutaneous, intravenous, intramuscular or intraperitoneal administration). They can be used for diagnostic purposes or are also suitable for biotechnological processes such as e.g. affinity purification of proteases or the removal of proteases from solutions of any kind.

Compounds of structure (I) are also especially suitable for coating or modifying the surface of macromolecular carriers in order to prevent or reduce coagulation at these carriers. These macromolecular carriers, in particular surfaces of medical objects and instruments such as e.g. hemodialyzers, oxygenators and their tube systems, preferably consist of polymethyl methacrylates, copolymers with polymethyl methacrylate and analogous plastic materials as defined in WO 98/46648 (Bucha and Nowak). Homo- and copolymers are used for this purpose, for the production of which at least one monomer type is used which comprises, in addition to a polymerizable double bond or a polycondensated functional group, a further carbonyl group in the form of a ketone or a carboxylic acid derivative that does not participate in the polymerization reaction. Preferably, the polymer comprises a recurring unit of the formula (A)

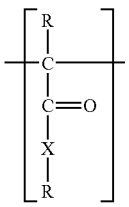

wherein the groups R can be the same or different and represent alkyl or aryl or a hydrogen atom. The alkyl group can be linear or branched and preferably consists of 1 to 20 carbon atoms. The aryl group preferably consists of 6 to 18, especially preferred 6 to 12 carbon atoms. The group X is optional and represents O, N or $CH_2$. In the case of X=N, N also carries another group R in addition to that indicated in formula (A), which is as defined above independently of the other groups R.

An especially preferred alkyl is a straight-chain or branched optionally substituted $C_{1-8}$ alkyl, for example a methyl, ethyl or propyl group. Examples of optionally present substituents include one or more halogen atoms, e.g. fluorine, chlorine, bromine or iodine atoms or hydroxyl groups, $C_{1-6}$ alkyl, or $C_{1-6}$ alkoxy or $C_{1-6}$ alkylthio groups. It is especially preferred that the aryl group be a monocyclic or bicyclic optionally substituted aryl which can optionally comprise one or more heteroatoms. Examples of such aryl groups include phenyl, 1- or 2-naphthyl, indenyl or isoindenyl groups. Examples of aryl groups comprising heteroatoms include $C_{3-9}$ heteroaryl groups comprising heteroatoms selected from oxygen, sulfur or nitrogen atoms. Monocyclic heteroaryl groups include for example pyrolyl, furyl, thienyl, imidazolyl, N-methylimidazolyl, N-ethylimidazoyly, benzothiazolyl, quinazolyl, naphthylpyridinyl, quinolyinyl, isoquinolinyl and tetrazolyl groups.

A preferred polymer comprising such groups is a polyalkyl methacrylate (PAMA) with an alkyl group preferably comprising 1 to 6 carbon atoms such as e.g. polymethyl methacrylate (PMMA), polyethylene methacrylate (PEMA) or polypropyl methacrylate. Furthermore, polyvinyl acetate, polycyclohexyl methacrylates or polyphenyl methacrylate can be used. Polymethyl methacrylate is especially preferred.

Copolymers or polymer mixtures in any proportions consisting of the above-mentioned polymers or of the polymers and one or more additional polymer components, for example polystyrene, polyacrylonitrile or polyamides, can be used. Preferably, the amount of monomers exhibiting a structural element (A) in such mixed polymers is at least 20%, especially preferred at least 40% and most preferred at least 60%.

For modifying such surfaces, the surface is contacted with the inhibitor conjugates of the present invention, e.g. in the form of a solution. Mixtures of different inhibitor conjugates of the present invention can also be used for this purpose.

Experimental Methods:
Abbreviations
ACN=acetonitrile
Amba=amidinobenzylamide
Cha=cyclohexylalanine
CKIBE=chloroformic acid isobutyl ester
DIEA=diisopropylethylamine
DMF=dimethylformamide
EE=acetic acid ethyl ester
AcOH=acetic acid
HBTU=2-(1H-benzotriazole-1-yl)-1,1,3,3-tetramethyluronium hexafluorophosphate
4-MeO-bs=4-methoxybenzenesulfonyl
4-MeO-3-Cl-bs=4-methoxy-3-chloro-benzenesulfonyl
4-MeO-3-Me-bs=4-methoxy-3-methyl-benzenesulfonyl
Mtr=4-methoxy-2,3,6-trimethyl-benzenesulfonyl
NMM=N-methyl morpholine
OSu=succinimide ester
OtBu=tert. butyl ester
PyBOP=benzotriazole-1-yl-oxy-tri-pyrrolidino-phosphonium hexafluorophosphate
TFA=trifluoroacetic acid
THF=tetrahydrofuran Analytic HPLC: Shimadzu LC-10A system, column: Vydac $C_{18}$, 5 μm (250×4 mm), solvent A: 0.1% TFA in water, B: 0.1% TFA in ACN, gradient: 10% B to 60% B in 50 min, 1 ml/min flow, detection at 220 or 215 nm.

Preparative HPLC: Shimadzu LC-8A system, column: Vydac $C_{18}$, 10 μm (250×22 mm), solvent A: 0.1% TFA in water, B: 0.1% TFA in ACN, gradient: 20% B to 65% B in 120 min, 10 ml/min flow, detection at 220 nm.

Mass Spectroscopy:
The mass spectra were measured on a Kompact Probe of the company Kratos (Manchester, England) with a time-of-flight detector and α-cyano-hydroxycinnamic acid as matrix.

Determination of the Kinetic Constants:
For determining the thrombin inhibiting effect of all reversibly binding inhibitors and inhibitor conjugates with inhibiting constants $\geq 1$ nM, 175 μl tris buffer (0.05 mM, 0.1 M NaCl, pH 7.8; contains the inhibitor) and 50 μl substrate (d-Phe-Gly-Arg-pNa in $H_2O$, concentrations in the preparation for the measurement 360, 120 and 60 μM) were mixed at room temperature and the reaction was started by adding 50 μl human α-thrombin (Kordia, final thrombin concentration in the preparation for the measurement 0.16 nM). The change in absorption at 405 nm was determined over a period of 5 minutes by means of a Microplate Reader (Labsystems iEMS Reader MF). After calculation of the increases (reaction rates), the $K_i$ values were determined according to Dixon (Biochem. J. 55, 170-171, 1953) by linear regression by means of a computer program. The $K_i$ values are the average values of at least three calculations.

The $K_i$ values for trypsin were determined analogously.

For determining the thrombin inhibiting effect of all reversibly binding inhibitors and inhibitor conjugates with inhibiting constants smaller than 1 nM, a fluorescence spectrometer (LS50B from the company Perkin Elmer) was used. The preparation for the measurement consists of 880 μl tris buffer (0.05 mM, 0.1 M NaCl, pH 7.8; contains the inhibitor, the inhibitor concentration in the preparation for the measurement is higher than 200 pM) and 100 µl substrate (Tos-Gly-Pro-Arg-AMC, concentrations in the measuring charge 5 to 30 µM). Measurement is started by adding 20 µl human α-thrombin (Kordia, final thrombin concentration in the measuring charge 21 pM). The increase in fluorescence intensity was observed over a period of 7 minutes ($\lambda_{Ex}$ 365 nm, $\lambda_{Em}$ 455 nm). After calculation of the increases (reaction rates), the $K_i$ values were determined according to Dixon (Biochem. J. 55, 170-171, 1953) by linear regression by means of a computer program. The Ki values are the average values of at least three calculations.

When slow-binding was observed for the inhibitors, the evaluation was carried out analogously to a previously described procedure (Steinmetzer et al., Potent bivalent thrombin inhibitors: Replacement of the scissile peptide bond at P1-P1' with arginyl ketomethylene isosteres. J. Med. Chem. (1999) 42, 3109-3115).

For optimizing the inhibitor conjugates, in particular of the following Examples 1 and 2, suitable groups $R_1$ were sought which allow as strong a thrombin inhibition as possible. For examining the selectivity of the compounds, the inhibiting constants for trypsin were determined as well. The higher the quotient [$Ki_{Trypsin}/Ki_{Thrombin}$], the more selectively the compound functions as a thrombin inhibitor. In order to facilitate the synthesis, this optimization was first carried out without coupling a polyalkylene glycol group to inhibitor molecules of formula (II) as listed in Table I. These compounds, which are active as thrombin inhibitors themselves, can be used as synthetic intermediates for the inhibitor conjugates of formula (I). As a central component, a glycyl-prolyl-dipeptide was consistently incorporated into the inhibitors.

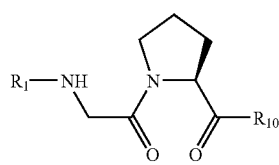
(II)

The results of the selectivity determination are shown in Table I for exemplary compounds, wherein $R_{10}$ in the compounds of the table has the structure

TABLE I

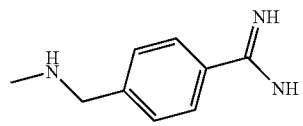

| No. | $R_1$ | $K_i$ Thrombin (nM) | $K_i$ Trypsin (nM) | $K_i$ Trypsin/ $K_i$ Thrombin |
|---|---|---|---|---|
| 1a | 4-methoxy-3-chloro-bs | 0.44 | 20 | 45 |
| 1b | 4-methoxy-3-methyl-bs | 0.64 | 13 | 20 |
| 1c | 4-methoxy-bs* | 0.97 | 22.7 | 23.4 |
| 2 | Mtr** | 1.3 | 15.7 | 12.1 |
| 3 | 3-methoxy-bs | 1.9 | 3 | 1.6 |
| 4a | 3,4-dichloro-bs | 2.5 | 5.8 | 2.3 |
| 4b | 3-methyl-bs | 2.8 | 8 | 2.9 |
| 5 | 3-chloro, 4-methyl-bs | 3.5 | 6.2 | 1.8 |
| 6 | benzylsulfonyl | 3.6 | 7.4 | 2.1 |
| 7 | 3-chloro-bs | 3.8 | 3.7 | 0.97 |
| 8 | 3,4-dimethoxy-bs | 4.7 | 19.6 | 4.2 |
| 9 | 2,4,5-trichloro-bs | 5.9 | 19.5 | 3.3 |
| 10 | 1-naphthylsulfonyl | 7.8 | 3.9 | 0.5 |
| 11 | 3,5-dichloro-bs | 8.5 | 3.4 | 0.4 |
| 12 | 2-naphthylsulfonyl | 8.5 | 58 | 6.8 |
| 13 | 4-chloro-bs | 10.0 | 27.3 | 2.7 |
| 14 | 2,4-dichloro, 5-methyl-bs | 10.5 | 11.8 | 1.1. |
| 15 | bs | 10.8 | 10.4 | 0.96 |
| 16 | pentamethyl-bs | 12.7 | 27.8 | 2.2 |
| 17 | 2,3-dichloro-bs | 12.7 | 11.1 | 0.87 |
| 18 | 2,3,5,6-tetramethyl-bs | 13.4 | 34.0 | 2.5 |
| 19 | 2,4,6-triisopropyl-bs | 13.5 | 9.1 | 0.67 |
| 20 | cyclohexylmethyl-sulfonyl | 13.6 | 3.1 | 0.22 |
| 21 | 2,4-dichloro-bs | 15.1 | 17.5 | 1.2 |
| 22 | 4-methyl-bs | 16.1 | 14.2 | 0.88 |
| 23 | 2,3,4-trichloro-bs | 16.4 | 11.7 | 0.71 |
| 24 | 2,4,6-trimethyl-bs | 16.6 | 13.4 | 0.80 |
| 25 | 2,4-dichloro, 6-methyl-bs | 16.9 | 19 | 1.1 |
| 26 | 4-ethyl-bs | 19.1 | 50.2 | 2.6 |
| 27 | 2-chloro-bs | 19.3 | 19.1 | 0.98 |
| 28 | Pbf*** | 30.3 | 37.1 | 1.2 |
| 29 | 4-tert. butyl-bs | 32.2 | 10.4 | 0.32 |
| 30 | 3-nitro-bs | 38.0 | 16.1 | 0.42 |
| 31 | phenylethylsulfonyl | 41.9 | 16.5 | 0.39 |
| 32 | trans-styrenesulfonyl | 44.3 | 2.1 | 0.05 |
| 33a | 3-cyano-bs | 48 | 22.5 | 0.47 |
| 33b | 4-ethoxy-bs | 66 | 28 | 0.42 |
| 34 | 4-cyano-bs | 76 | 24.9 | 0.33 |
| 35 | 4-nitro-bs | 115 | 12.6 | 0.11 |

*bs = benzene sulfonyl
**Mtr = 2,3,6-trimethyl-4-methoxy-bs
***Pbf = 2,2,4,6,7-pentamethyldihydrobenzofuran-5-sulfonyl Compounds with the structure (II), wherein $R_1$ represents a 4-methoxy-3-chloro-benzenesulfonyl, 4-methoxy-3-methyl-benzenesulfonyl, 4-methoxy-benzenesulfonyl or 4-methoxy-2,3,6-trimethyl-phenylsulfonyl group and $R_{10}$ is

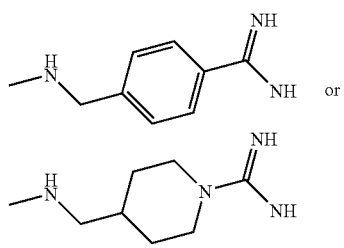

turned out to be especially suitable thrombin inhibitors with good trypsin selectivity.

Based on these experiments, the glycine was replaced with trifunctional amino acids. Selectivity values for the resulting compounds with the structure (III) that were obtained analogously to the values given in Table I are listed in Table II. In column 3, those acid and amino acid groups are listed that are formed by $R_9$ together with the amino group on the adjacent carbon atom and the carbonyl group which forms an amide bond with the nitrogen of the heterocycle. In the compounds of Table II as well, $R_{10}$ represents

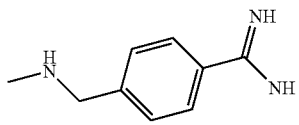

Especially suitable compounds with the structure (III), which are active thrombin inhibitors themselves, are also embraced by this application as synthetic intermediates.

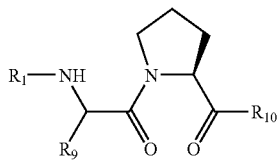

(III)

This applies in particular to compounds with the structure (III) in which
$R_1$ represents a 4-methoxy-3-chloro-benzenesulfonyl, 4-methoxy-3-methyl-benzenesulfonyl, 4-methoxy-phenylsulfonyl or 4-methoxy-2,3,6-trimethyl-phenylsulfonyl group, $R_9$ represents one of the groups —$(CH_2)_j$—$C(O)OR_{11}$, —$(CH_2)_j$—$R_{12}$ or —$(CH_2)_j$—$C(O)NH$-$R_{11}$, wherein $R_{11}$ is a hydrogen atom, or $C_1$—$C_6$ alkyl, $C_7$—$C_{13}$ aralkyl or $C_6$—$C_{12}$ aryl, which can optionally be substituted, $R_{12}$ is one of the groups $NH_2$, OH or SH and j is 1, 2, 3 or 4, $R_{10}$ is

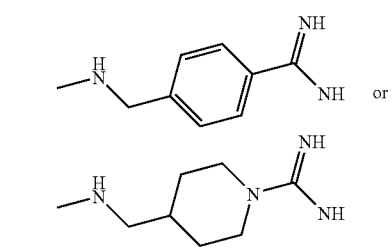

and an L-configuration is present at the carbon atom marked with *.

Suitable substituents for $R_{11}$ are halogen atoms such as e.g. chlorine or bromine, linear or branched alkyl groups, carboxyl groups, cyano groups, carboxyalkyl groups or aminoalkyl groups, which in the case of the aralkyl group can be present at the aromatic but also at the alkyl portion.

Exemplary compounds of formula (III) are listed in Table 2 together with their selectivity values.

TABLE 2

| No. | $R_1$ | —NH—$CHR_9$—CO— | $K_i$ Thrombin (nM) | $K_i$ Trypsin (nM) | $K_i$ Trypsin/ $K_i$ Thrombin |
|---|---|---|---|---|---|
| 36 | 2-naphthylsulfonyl | Asp(OBzl) | 1.3 | 17.6 | 13.6 |
| 37 | 2-naphthylsulfonyl | diaminopropionic acid | 2.4 | 10.3 | 4.3 |
| 38 | 2-naphthylsulfonyl | Ser | 2.54 | 27.6 | 10.9 |
| 39 | 2-naphthylsulfonyl | Asn | 3.4 | 37.4 | 11 |
| 40 | 2-naphthylsulfonyl | Gln | 3.8 | 16.1 | 4.2 |
| 41 | 2-naphthylsulfonyl | Thr | 5.24 | 54.5 | 10.4 |
| 12 | 2-naphthylsulfonyl | Gly | 8.5 | 58 | 6.8 |
| 42 | 2-naphthylsulfonyl | Asp | 24.1 | 69 | 2.9 |
| 43 | 2-naphthylsulfonyl | D-Asn | 52.5 | 22.4 | 0.42 |
| 44 | 4-methoxy-bs | Asn(4-cyano-benzyl) | 0.045 | 41 | 911 |
| 45 | 4-methoxy-bs | Asn(4-aminomethyl-benzyl) | 0.061 | 39 | 639 |
| 46 | 4-methoxy-bs | Asn(3-cyano-benzyl) | 0.061 | 71 | 1163 |
| 47 | 4-methoxy-bs | Asn(benzyl) | 0.065 | 39 | 600 |
| 48 | 4-methoxy-bs | Asn(3-aminomethyl-benzyl) | 0.08 | 41 | 512 |
| 49 | 4-methoxy-bs | Asp(OBzl) | 0.21 | 38 | 181 |
| 50 | 4-methoxy-bs | Asn | 0.36 | 53 | 147 |
| 51 | 4-methoxy-bs | Ser | 0.255 | 17 | 67 |
| 52 | 4-methoxy-bs | Asp(OMe) | 0.68 | 21.4 | 31 |
| 53 | 4-methoxy-bs | Lys | 0.73 | 82 | 112 |
| 1c | 4-methoxy-bs | Gly | 0.97 | 22.7 | 23.4 |
| 55 | 4-methoxy-bs | Asp | 1.6 | 77 | 48 |

EXAMPLES

Example 1

Preparation of 4-methoxy-benzenesulfonyl-Asn(PEG$_{2000}$-OMe)-Pro-4-amidinobenzylamide (the synthesis of the compound is illustrated in more detail in FIG. 1 below):

A) Z-Pro-4-(cyano)benzylamide 7.27 g (29.16 mmol) Z-Pro-OH and 3.2 ml (29.16 mmol) NMM were dissolved under stirring in 200 ml THF. Then the mixture was cooled to −15° C. and 3.79 ml (29.16 mmol) CKIBE were added. After about 10 minutes at −15° C., 4.24 g (32 mmol) 4-(cyano)benzylamine were added and stirring was continued for one hour at −15° C. and for another 12 hours at room temperature. The solvent was removed under vacuum; the residue was dissolved in 500 ml EE, and washed three times with 5% $KHSO_4$ solution, one time with an NaCl-saturated solution, three times with an $NaHCO_3$-saturated solution and three times with an NaCl-saturated solution, dried with $Na_2SO_4$ and concentrated in a vacuum.

Yield: 9.9 g (27.2 mmol) oil, 93%, HPLC: 31.67 min

B) Z-Pro-4(acetyl-oxamidino)benzylamide 9.5 g (26.1 mmol) Z-Pro-4-(cyano)benzylamide were dissolved in 300 ml methanol and 3.1 g (45 mmol) hydroxylamine hydrochloride and 7.83 ml (45 mmol) DIEA were added under stirring. The mixture was refluxed for 4 hours and left over night at room temperature. The precipitated intermediate product (HPLC 18.18 min) was filtered with suction, dried under vacuum, dissolved in 200 nm AcOH at room temperature and 75 mmol acetanhydride were added in three portions. After 30 minutes, the solvent and excess acetanhydride were removed under vacuum and the remaining residue was dissolved in EE. It was washed three times with 5% $KHSO_4$ solution and three times with an NaCl-saturated solution, which causes the product to precipitate as a solid substance which was filtered with suction, washed with water on the frit and dried in a vacuum.

Yield: 6.4 g (14.6 mmol) 56%; white crystals, HPLC: 24.37 min

C) H-Pro-4(amidino)benzylamide×2 HCl 6 g (13.6 mmol) Z-Pro-4(acetyl-oxamidino)benzylamide are dissolved under stirring in 200 ml 90% AcOH and 0.5 g 10% palladium on activated carbon were added in a protective gas atmosphere. Then hydrogenation is carried out for 12 hours with hydrogen and the catalyst is filtered off. The filtrate is concentrated in a vacuum, the residue is dissolved in 100 ml 0.5 N HCl and then again concentrated in a vacuum and dried.

Yield: 3.3 g (10.3 mmol) 76% solids, HPLC: 11.3 min (start at 0% B)

D) 4-MeO-benzenesulfonyl-Asp-OtBu 10 g (52.8 mmol) H-Asp-OtBu (Novabiochem) were suspended under stirring in 250 ml $H_2O$ and 150 ml ACN at room temperature and 13 ml (75 mmol) DIEA were added. The mixture was cooled in an ice bath. Then 11.7 g (55 mmol) 4-methoxy-benzenesulfonylchloride dissolved in 100 ml ACN were added drop-wise within one hour. During this time period, the pH value was monitored and adjusted to 8-9 by adding additional DIEA. Then the mixture was stirred for another 6 hours at room temperature and at a pH value of 8-9. Then the solvent was removed under vacuum and the remaining residue was dissolved in 300 ml water at a pH value of about 9. The aqueous phase was extracted twice with ether and subsequently the pH value was adjusted to about 3 by adding a 5% solution of $KHSO_4$. The acidic aqueous phase was then extracted three times with EE, the combined EE phase was then again washed twice with a 5% solution of $KHSO_4$ and three times with a saturated NaCl solution and dried with $Na_2SO_4$. Then the EE was removed under vacuum, the remaining oil was dissolved in hot EE and covered with a layer of hexane. The product crystallized at about 4° C.

Yield: 13.6 g, HPLC at 28.9 min

E) 4-MeO-bs-Asn($PEG_{2000}$-OMe)-OtBu 5 g (about 2.5 mmol) amino-$PEG_{2000}$-monomethylether (Rapp Polymere, Tübingen) and 2.7 g (7.5 mmol) 4-MeO-bs-Asp-OtBu were dissolved in 200 ml DMF and 50 ml ACN at room temperature and then cooled in an ice bath. Then 2.84 g (7.5 mmol) HBTU and 3.48 ml (20 mmol) DIEA were added and the mixture was stirred for 30 minutes while being cooled in an ice bath and then another 5 hours at room temperature. The solvent was concentrated under vacuum and the remaining residue was dissolved in a small amount of hot methanol and a large excess amount of ether was added. The mixture was left in an ice bath for one hour, and then the precipitated product was filtered with suction, washed with ether and dried. The solid substance is again dissolved in a small amount of hot methanol and a large excess amount of isopropanol is added. While the mixture is left in an ice bath, the product precipitates and is then withdrawn, washed with isopropanol on the frit and then dried in a vacuum. The compound is dried and used in that form for further synthesis.

Yield: 5.5 g, HPLC 35.1 min

F) 4-MeO-bs-Asn($PEG_{2000}$-OMe)-OH 5 g 4-MeO-bs-Asn($PEG_{2000}$-OMe)-OtBu were dissolved at room temperature in 150 ml 1 N HCl in acetic acid, the mixture was left at room temperature for 4 hours and then the solvent was removed under vacuum. The residue is dissolved in toluene, and the solvent is again evaporated under vacuum in order to remove traces of acid. This step is repeated twice, the residue is dissolved in some hot methanol and the product is precipitated with ether in a cold atmosphere. After filtering with suction and washing with ether, the product is dried in a vacuum and used in that form for further synthesis.

Yield: 4.7 g, HPLC 30.5 min

G) 4-Methoxy-benzenesulfonyl-Asn($PEG_{2000}$-OMe)-Pro-4-amidinobenzylamide 2 g (about 0.9 mmol) 4-MeO-bs-Asn($PEG_{2000}$-OMe)-OH and 0.57 g (1.8 mmol) of the H-Pro-4-amidinobenzylamide×2 HCl described in step C) are dissolved under stirring in 50 ml DMF. After cooling in an ice bath, 0.94 g (1.8 mmol) PyBOP and 0.93 ml (5.4 mmol) DIEA are added. The mixture was stirred for 30 minutes while being cooled in an ice bath and then another 4 hours at room temperature, the solvent was concentrated in a vacuum and the remaining residue was separated on Biogel P2 (company Biorad) with 2% acetic acid as eluting agent. The fractions containing the product were combined, concentrated in a vacuum and lyophilized from 80% tert. butanol. In a second step, the product was subsequently separated by means of ion-exchange chromatography on Fractogel EMD $COO^-$ or Source 30S with an ammonium acetate gradient and the combined fractions were lyophilized three times.

HPLC: 30.66 min

Example 2

Analogously to Example 1, the following compounds were synthesized using amino-PEG compounds with different molecular weights for the synthesis.

4-MeO-bs-Asn($PEG_{5000}$-OMe)-Pro-4-amidinobenzylamide
4-MeO-bs-Asn($PEG_{10000}$-OMe)-Pro-4-amidinobenzylamide
4-MeO-bs-Asn($PEG_{20000}$-OMe)-Pro-4-amidinobenzylamide
Mtr-Asn($PEG_{2000}$-OMe)-Pro-4-amidinobenzylamide
Mtr-Asn($PEG_{5000}$-OMe)-Pro-4-amidinobenzylamide
Mtr-Asn($PEG_{10000}$-OMe)-Pro-4-amidinobenzylamide
Mtr-Asn($PEG_{20000}$-OMe)-Pro-4-amidinobenzylamide By using the bifunctionalized amino-PEG, the following two compounds were prepared wherein the connecting line in these and the following formulas represents the linkage of the two inhibitor units by means of the indicated bifunctional polyalkylene glycol.

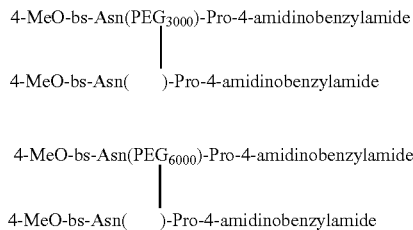

The following compounds were prepared using aminomethyl crown ethers:
4-MeO-bs-Asn(CH$_2$-crown5)-Pro-4-amidinobenzylamide
4-MeO-bs-Asn(CH$_2$-crown6)-Pro-4-amidinobenzylamide Example 3

Preparation of D-N(CH$_2$—CO—NH-PEG$_{2000}$-OMe)Cha-Pro-4-amidinobenzylamide (The synthesis of the target compound is illustrated in more detail in FIG. 2 below.):

A) D-N(benzyloxycarbonylmethyl)Cha-OtBu

The starting material D-N(benzyloxycarbonylmethyl)Cha-OtBu was prepared according to the method described in the literature (Preville et al., Bioorganic & Medicinal Chemistry Letters 7, 1563-1566 (1997).

B) D-N(carboxymethyl)Cha-OtBu×acetate 3.75 g (10 mmol) D-N(benzyloxycarbonylmethyl)Cha-OtBu were hydrogenated as usual in a mixture of 100 ml methanol, 5 ml acetic acid and 5 ml H$_2$O at room temperature and normal pressure for 3 hours with 0.3 g 10% Pd/C as catalyst. The catalyst was filtered off and the filtrate was concentrated under vacuum three times in admixture with toluene. The remaining substance is dissolved in 15 ml acetic acid and precipitated by adding 200 ml diethylether (white solid).

C) Z-D-N(carboxymethyl)Cha-OtBu×cyclohexylamine 2 g (5.8 mmol) D-N(carboxymethyl)Cha-OtBu×acetate were suspended in 75 ml water, 15 ml 1 N NaOH and 75 ml dioxane under vigorous stirring and cooled in an ice bath. Then 7 mmol Z-Cl dissolved in 30 ml dioxane were added drop-wise within 30 minutes and stirring was continued for 30 minutes in an ice bath and for another 12 hours at room temperature. The pH value was repeatedly adjusted to about 9-10 by adding 1 N NaOH. Then the solvent was removed in a vacuum and the residue was taken up in EE and water, washed three times with a 5% solution of KHSO$_4$ and three times with a saturated NaCl solution, dried with Na$_2$SO$_4$ and concentrated in a vacuum. The oily residue was dissolved in ether and crystallized as cyclohexylamine salt, filtered with suction and dried under vacuum.

D) Z-D-N(CH$_2$—CO—NH-PEG$_{5000}$-OMe)Cha-OtBu 0.62 g (1.2 mmol) Z-D-N(carboxymethyl)Cha-OtBu×cyclohexylamine were suspended in 200 ml EE and washed three times with 50 ml of a 5% solution of KHSO$_4$ and three times with a saturated NaCl solution, dried with Na$_2$SO$_4$ and concentrated in a vacuum. The oily residue and 2 g (0.4 mmol) amino-PEG$_{5000}$-OMe were dissolved under stirring in 100 ml DMF and cooled in an ice bath. 0.62 g (1.2 mmol) PyBOP and 3 mmol DIEA were added and the mixture was stirred for 30 minutes while being cooled in an ice bath and then another 12 hours at room temperature. The solvent was evaporated under vacuum, the residue was dissolved in a small amount of hot methanol and precipitated with isopropanol in a cold atmosphere, filtered with suction and dried under vacuum. The solid was again dissolved in a small amount of hot methanol and precipitated with ether in a cold atmosphere, filtered with suction and dried under vacuum (solid).

Yield: 1.9 g

E) Z-D-N(CH$_2$—CO—NH-PEG$_{5000}$-OMe)Cha-OH

The tert. butyl ester was cleaved off as described in Example 1F.

Yield: 1.7 g (solid)

F) Z-D-N(CH$_2$—CO—NH-PEG$_{50000}$—OMe)Cha-Pro-4-(amidino)benzylamide

The H-Pro-4(amidino)benzylamide×2 HCl prepared in Example 1C was coupled to 1 g Z-D-N(CH$_2$—CO—NH-PEG$_{5000}$-OMe)Cha-OH according to the process described in Example 1G. The product was first precipitated with isopropanol and then with ether, filtered with suction and dried under vacuum (crude product: 0.9 g).

G) H-D-N(CH$_2$—CO—NH-PEG$_{5000}$-OMe)Cha-Pro-4-(amidino)benzylamide 0.9 g Z-D-N(CH$_2$—CO—NH-PEG$_{5000}$-OMe)Cha-Pro-4-(amidino)benzylamide were hydrogenated for 4 hours as described in Example 1C, and after filtering off the catalyst and concentrating the solvent in a vacuum, the residue was dissolved in a small amount of hot methanol, precipitated with a large amount of ether and filtered with suction. The precipitated crude product was purified on Biogel P2 with 2% AcOH as eluting agent. In a second step, the product was subsequently separated by means of ion-exchange chromatography on Fractogel EMD COO$^-$ or Source 30S with an ammonium acetate gradient and the combined fractions were lyophilized three times.

Example 4

Analogously to Example 3, the following compounds were synthesized using amino-PEG compounds with different molecular weights for the synthesis.
H-D-N(CH$_2$—CO—NH-PEG$_{2000}$-OMe)Cha-Pro-4-(amidino)benzylamide
H-D-N(CH$_2$—CO—NH-PEG$_{10000}$-OMe)Cha-Pro-4-(amidino)benzylamide
H-D-N(CH$_2$—CO—NH-PEG$_{20000}$-OMe)Cha-Pro-4-(amidino)benzylamide By using a bifunctionalized amino-PEG, the following compounds were prepared:

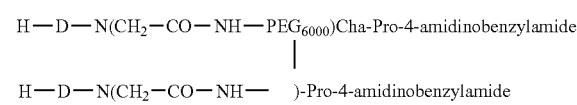

The following compounds were prepared using aminomethyl crown ethers:
H-D-N(CH$_2$—CO—NH—CH$_2$-crown5)-Pro-4-amidinobenzylamide
H-D-N(CH$_2$—CO—NH—CH$_2$-crown6)-Pro-4-amidinobenzylamide Example 5

D-N(CH$_2$—CO—NH-PEG$_{5000}$-OMe)Cha-Pro-4-(amidomethyl)N(amidino)benzylamide (The synthesis of the target compound is illustrated in more detail in FIG. 3 below):

A) 4-(Trifluoroacetyl-aminomethyl)-piperidine 166 mmol (18.95 g, 19.91 ml) 4-aminomethyl piperidine were dissolved in 100 ml DCM and cooled in an ice bath using a magnetic stirrer. 182.6 mmol (25.94 g, 21.78 ml) trifluoroacetic acid ethyl ester are added drop-wise within one hour. Then the mixture is cooled for another hour in an ice bath and subsequently stirred at room temperature for 5 hours. The product precipitating during the reaction is filtered with suction.

Yield: 18.68 g=53.55%

MS: calculated, 210.17; found, 211.3 [M+H]$^+$(Maldi)

TLC: Rf n-butanol/glacial acetic acid/water 4/1/1=0.51

B) 4-(Trifluoroacetyl-aminomethyl)-N(benzyloxycarbonyl)-piperidine 14.89 ml (85.6 mmol) DIEA are added to a solution of 18 g (85.6 mmol) 4-trifluoroacetyl-amidomethyl)-piperidine in 150 ml DMF. While stirring this mixture in an ice bath, 22.36 g (89.75 mmol) Z-Osu are added, which was first dissolved in 75 ml DMF. The mixture is stirred in an ice bath for one hour and then at room temperature for 7 hours. Then the solvent is concentrated under vacuum and the remaining residue is collected in ethyl acetate and washed three times with a 5% solution of $KHSO_4$ and three times with a saturated NaCl solution. The EE phase is dried over $Na_2SO_4$ and the solvent is concentrated. Recrystallization from ethyl acetate/hexane (white crystals).

Yield: 28.15 g=95.52%

MS: calculated, 344.27; found, 345.1

TLC: Rf n-butanol/glacial acetic acid/water 4/1/1=0.83 benzene/acetone/glacial acetic acid 27/10/0.5=0.73

C) 4-(Aminomethyl)-N(benzyloxycarbonyl)-piperidine 27.5 g (79.88 mmol) 4-(trifluoroacetyl-aminomethyl)-N(benzyloxycarbonyl)-piperidine are dissolved in 150 ml dioxane and 150 ml 1 N NaOH solution are added. The mixture is stirred for 3 hours at 40° C. and then the solvent is concentrated under vacuum. The residue is collected in water and extracted three times with DCM. The combined DCM phases are dried over $Na_2SO_4$ and then the solvent is concentrated under vacuum.

Yield: 13.92 g oil, 56.09 mmol=70.2%

MS: calculated, 248.13; found, 249.3 [M+H]$^+$

D) Boc-Pro-4-(amidomethyl)-N(benzyloxycarbonyl)-piperidine 0.86 g Boc-Pro-OH are dissolved in 60 ml absolute THF using a magnetic stirrer and 0.44 ml (4 mmol) NMM are added. The mixture is cooled to −15° C. and 4 mmol (0.52 ml) CKIBE are added. After another 10 minutes of stirring at −15° C., 1.1 g (4.4 mmol) 4-(aminomethyl)-N(benzyloxycarbonyl)-piperidine are added and the mixture is stirred for another hour at −15° C. and at room temperature overnight. The solvent is concentrated in a vacuum and the remaining residue is collected in ethyl acetate and washed three times with a 5% solution of $KHSO_4$, once with a saturated NaCl solution, three times with a saturated $NaHCO_3$ solution and again three times with a saturated NaCl solution. Then the ethyl acetate phase is dried with $Na_2SO_4$ and concentrated.

Recrystallization from ethyl acetate/hexane.

Yield: 1.5 g, 3.3 mmol (82.5%)

E) Boc-Pro-4-(amidomethyl)piperidine×acetate 1 g (2.2 mmol) Boc-Pro-4-(amidomethyl)-N(benzyloxycarbonyl)-piperidine are hydrogenated in glacial acetic acid analogously to Example 1C with 150 mg Pd/C as catalyst. The catalyst is filtered off and the solvent is largely concentrated under vacuum, and the product is precipitated by adding diethyl ether.

Yield: 0.6 g

F) Boc-Pro-4-(amidomethyl)-N(amidino)piperidine×TFA 0.5 g (1.34 mmol) Boc-Pro-4-(amidomethyl)piperidine× acetate are stirred at room temperature for 24 hours with 0.4 g (2.7 mmol) pyrazole-carboxamidine-hydrochloride and 0.7 ml (4 mmol) DIEA in 4 ml DMF. The DMF is removed under vacuum and the residue is separated from salts and unreacted pyrazole-carboxamidine-hydrochloride by means of preparative reversed-phase HPLC.

Yield: 0.35 g

G) H-Pro-4-(amidomethyl)-N(amidino)piperidine×2 HCl 5 ml 1 N HCl/glacial acetic acid are poured over 0.3 g (0.64 mmol) Boc-Pro-4-(amidomethyl)-N(amidino)piperidine× TFA and the mixture is left at room temperature for one hour. The glacial acetic acid is largely concentrated in a vacuum and the residue is precipitated by adding diethyl ether. The product is filtered with suction, washed with more diethyl ether and dried under vacuum.

Yield: 0.18 g

H) Z-D-N($CH_2$—CO—NH-$PEG_{5000}$-OMe)Cha-Pro-4-(amidomethyl)-N(amidino)piperidine×HCl 0.15 g (0.46 mmol) of the H-Pro-4-(amidomethyl)-N(amidino)piperidine×2 HCl prepared in Example 5G was coupled to 1 g Z-D-N($CH_2$—CO—NH-$PEG_{5000}$-OMe)Cha-OH according to the process described in Example 1G by means of PyBOP/DIEA. The product was precipitated first with isopropanol and then with ether, filtered with suction and dried under vacuum (crude product: 0.9 g).

I) D-N($CH_2$—CO—NH-$PEG_{5000}$-OMe)Cha-Pro-4-(amidomethyl)-N(amidino)piperidine×2 HCl 0.8 g Z-D-N($CH_2$—CO—NH-$PEG_{5000}$-OMe)Cha-Pro-4-(amidomethyl)-N(amidino)piperidine×HCl are hydrogenated in 90% acetic acid analogously to the process of 1 C. The product is precipitated from methanol/ether and purified on Biogel P2 and ion-exchange chromatography (Fractogel EMD $COO^-$ or Source 30S) and lyophilized.

Yield: 0.46 g

Example 6

Analogously to Example 5, the following compounds were synthesized using amino-PEG compounds with different molecular weights for the synthesis.

H-D-N($CH_2$—CO—NH-$PEG_{2000}$-OMe)Cha-Pro-4-(amidomethyl)-N(amidino)piperidine×2 HCl H-D-N($CH_2$—CO—NH-$PEG_{10000}$-OMe)Cha-Pro-4-(amidomethyl)-N(amidino)piperidine×2 HCl H-D-N($CH_2$—CO—NH-$PEG_{20000}$-OMe)Cha-Pro-4-(amidomethyl)-N(amidino)piperidine×2 HCl By using a bifunctionalized amino-PEG, the following compounds were prepared:

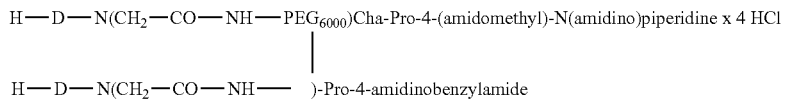

H—D—N(CH$_2$—CO—NH—PEG$_{6000}$)Cha-Pro-4-(amidomethyl)-N(amidino)piperidine x 4 HCl
|
H—D—N(CH$_2$—CO—NH— )-Pro-4-amidinobenzylamide The following compounds were prepared using aminomethyl crown ethers:
H-D-N(CH$_2$—CO—NH—CH$_2$-crown5)-Pro-4-(amidomethyl)-N(amidino)piperidine×2 HCl
H-D-N(CH$_2$—CO—NH—CH$_2$-crown6)-Pro-4-(amidomethyl)-N(amidino)piperidine×2 HCl Example 7

Preparation of D-N(CH$_2$—CO—NH-PEG$_{2000}$-OMe)Cha-Pro-Arg-CH$_2$Cl (The synthesis of the target compound is illustrated in more detail in FIG. 4 below.):

A) H-Arg-(Pbf)-CH$_2$—Cl×HCl

Boc-Arg(Pbf)-CH$_2$—Cl was prepared analogously to the method described in the literature for Boc-Arg(Z$_2$)—CH$_2$—Cl (Steinmetzer et al., 1999 *J. Med. Chem.* 42, 3109-3115). By adding 75 ml 1 N HCl in glacial acetic acid to 5 g Boc-Arg(Pbf)-CH$_2$—Cl, the Boc group was cleaved off selectively, the solvent was largely removed in a vacuum, and the product was precipitated by adding cold diethyl ether, filtered with suction and dried under vacuum.
Yield: 3.7 g B) Boc-d-Cha-Pro-OH The compound is prepared according to the synthesis strategy described in the literature (Steinmetzer et al., 1999 *J. Med. Chem.* 42, 3109-3115).

C) Boc-d-Cha-Pro-Arg(Pbf)-CH$_2$—Cl

From 3 g (8.14 mmol) Boc-d-Cha-Pro-OH, 0.9 ml (8.14 mmol) NMM and 1.06 ml (8.14 mmol) CKIBE in 100 ml THF, the mixed anhydride is formed at −15° C. After 10 minutes, 4.03 g (8.14 mmol) H-Arg(Pbf)-CH$_2$—Cl×HCl are added and the mixture is stirred for another hour at −15° C. and overnight at room temperature and then processed as described in Example 1A.
Yield: 4.6 g (5.7 mmol)

D) H-d-Cha-Pro-Arg(Pbf)-CH$_2$—Cl×HCl

The Boc group is cleaved off analogously to the process of Example 5G, the product is precipitated with ether, filtered with suction and dried under vacuum.
Yield: 3.86 g (5.2 mmol)

E) H-d-N(CH$_2$—CO-OtBut)Cha-Pro-Arg(Pbf)-CH$_2$—Cl×HCl 3 g (4 mmol) H-d-Cha-Pro-Arg(Pbf)-CH$_2$—Cl×HCl are dissolved in 100 ml DMF and 0.74 ml (4.15 mmol) bromoacetic acid tert. butyl ester and 1.16 g (5 mmol) silver(I) oxide are added at room temperature. The mixture is stirred overnight and then the precipitated silver salts are centrifuged off. The DMF is removed under vacuum; the residue is collected in ethyl acetate and washed twice with NaCl-saturated water, dried with Na$_2$SO$_4$ and concentrated.
Yield: 2.7 g (3.1 mmol) crude product F) H-d-N(CH$_2$—COOH)Cha-Pro-Arg-CH$_2$—Cl×2 trifluoroacetic acid 2.5 g (2.87 mmol) of the crude product H-d-N(CH$_2$—CO-OtBut)Cha-Pro-Arg(Pbf)-CH$_2$—Cl×HCl are mixed at room temperature with 50 ml 90% trifluoroacetic acid in water and stirred for 1.5 hours at room temperature. The solvent is largely removed under vacuum and the residue is precipitated with cold diethyl ether. The crude product is filtered with suction, washed with ether, dried and purified with preparative reversed-phase HPLC.

G) H-d-N(CH$_2$—CONH-PEG$_2$000-OMe)Cha-Pro-Arg-CH$_2$—Cl×2 trifluoroacetic acid 40 mg (0.054 mmol) HPLC-purified H-d-N(CH$_2$—COOH)Cha-Pro-Arg-CH$_2$—Cl×2 trifluoroacetic acid and 80.75 mg (0.04 mmol) amino-PEG$_{2000}$-OMe are dissolved in 3 ml DMF, and while the mixture is cooled in an ice bath, 57 μl propanephosphonic acid anhydride and 55 μl DIEA are added. After one hour, the ice bath is removed and the mixture is stirred for 3 more hours at room temperature. The solvent is removed under vacuum and the residue is purified by means of preparative reversed-phase chromatography.
Yield: 45 mg Example 8

Determination of the Kinetic Constants

With the exception of the compound described in Example 6, all inhibitors are reversibly binding thrombin inhibitors. The K$_i$ values determined only depend to the chain length of the PEG to a certain extent; therefore, only one inhibitor and its K$_i$ value are exemplary given for each type of compound and as a reference, the kinetic constants of the compounds with a free carboxyl group that are not bonded to a PEG chain are indicated.

Kinetic Constant for the Reversibly Binding Inhibitor of Example 1/2
4-Methoxy-benezenesulfonyl-Asn(PEG$_{2000}$-OMe)-Pro-4-amidinobenzylamide
Ki$_{Thrombin}$: 0.53 nM; Ki$_{Trypsin}$: 92.53 nM; Ki$_{Trypsin}$/Ki$_{Thrombin}$: 174

Reference: 4-Methoxy-benezenesulfonyl-Asp-Pro-4-amidinobenzylamide
Ki$_{Thrombin}$: 1.6 nM; Ki$_{Trypsin}$: 77 nM; Ki$_{Trypsin}$/Ki$_{Thrombin}$: 48

In inhibitors of this type, the incorporation of the PEG chain leads to an improved thrombin inhibition compared to the reference compound, as well as to an improved selectivity towards trypsin.

4-Methoxy-benezenesulfonyl-Asn(4-[MeO-PEG$_{5000}$-CH$_2$CH$_2$CO—NHCH$_2$]-benzyl-Pro-4-amidinobenzylamide
Ki$_{Thrombin}$: 0.19 nM Reference: 4-Methoxy-benezenesulfonyl-Asp-Pro-4-amidinobenzylamide
Ki$_{Thrombin}$: 1.6 nM 4-Methoxy-benzenesulfonyl-Lys(propionyl-PEG$_{5000}$-OMe)-Pro-4-amidinobenzylamide
Ki$_{Thrombin}$: 0.95 nM; Ki$_{Trypsin}$: 61 nM; Ki$_{Trypsin}$/Ki$_{Thrombin}$: 64

Reference: 4-Methoxy-benezenesulfonyl-Lys-Pro-4-amidinobenzylamide
Ki$_{Thrombin}$: 0.73 nM; Ki$_{Trypsin}$: 82 nM; Ki$_{Trypsin}$/Ki$_{Thrombin}$: 112

Kinetic Constant for the Reversibly Binding Inhibitor of Example 3/4

H-D-N(CH$_2$—CO—NH-PEG$_{5000}$-OMe)Cha-Pro-4-(amidino)benzylamide

Ki$_{Thrombin}$: 0.97 nM; Ki$_{Trypsin}$: 3.4 nM; Ki$_{Trypsin}$/Ki$_{Thrombin}$: 3.5

Reference: H-D-N(CH$_2$—COOH)Cha-Pro-4-(amidino)benzylamide (This reference compound, which is not PEG-coupled, is identical to the inhibitor H317/86 described by the company Astra; Gustafsson et al., 1998 *Thromb. Hemost.* 79, 110-118).

Ki$_{Thrombin}$: 0.3 nM; Ki$_{Trypsin}$: 3.6 nM; Ki$_{Trypsin}$/Ki$_{Thrombin}$: 12

In inhibitors of this type, the incorporation of the PEG chain leads to a slight deterioration of the thrombin inhibition while the trypsin inhibition remains unaffected.

Kinetic Constant for the Reversibly Binding Inhibitor of Example 5 and 6

H-D-N(CH$_2$—CO—NH-PEG$_{5000}$-Me)Cha-Pro-4-(amidomethyl)-N(amidino)piperidine

Ki$_{Thrombin}$: 2.4 nM; Ki$_{Trypsin}$: 239 nM; Ki$_{Trypsin}$/Ki$_{Thrombin}$: 100

Reference: H-D-N(CH$_2$—COOH)Cha-Pro-4-(amidomethyl)-N(amidino)piperidine

Ki$_{Thrombin}$: 1.3 nM; Ki$_{Trypsin}$: 266 nM; Ki$_{Tyrpsin}$/Ki$_{Thrombin}$: 173

In inhibitors of this type as well, the incorporation of the PEG chain leads to a slight deterioration of the thrombin inhibition while the trypsin inhibition remains largely unaffected.

Kinetic Constant for the Reversibly Binding Inhibitor of Example 7

The following kinetic constants were determined according to the method described in the literature (Stein and Trainor, 1986 *Biochemistry* 25, 5414-5419).

H-d-N(CH$_2$—CONH-PEG$_{2000}$-OMe)Cha-Pro-Arg-CH$_2$—Cl×2 trifluoroacetic acid:

Ki$_i$=10.6 nM; k$_{inact}$=0.08 s$^{-1}$; K$_{inact}$/K$_i$=7.5×10$^6$ M$^{-1}$s$^{-1}$ As a reference, the analogous non-PEG-coupled compound was measured:

Ki$_i$=3.8 nM; k$_{inact}$=0.079 s$^{-1}$; K$_{inact}$/K$_i$=2.1×10$^7$ M$^{-1}$s$^{-1}$ The data for the chloromethyl ketone lead structure D-Phe-Pro-Arg-CH$_2$—Cl (PPACK) were taken from the literature (Walker et al., 1985 *Biochem. J.* 230, 645-650):

Ki$_i$=25 nM; k$_{inact}$=0.11 s$^{-1}$; K$_{inact}$/K$_i$=4.4×10$^6$ M$^{-1}$s$^{-1}$ The PEG-coupled compound is somewhat less active than the analogous free compound; on the other hand, however, it is a stronger thrombin inhibitor than the PPACK already described in the literature.

Example 8a

Preferably, effective thrombin inhibitors should hardly inhibit the plasmolytic enzymes plasmin, urokinase and tPA since these proteases participate in the disintegration of fibrin clots and therefore possess antithrombotic properties. For this reason, two selected representatives of the inhibitors without PEG described in Tables 1 and 2 and one PEG-coupled inhibitor were examined with respect to their inhibiting effect on these enzymes.

Inhibiting constants of selected inhibitors with respect to the enzymes thrombin, plasmin, urokinase and tPA (values given in nM).

| No. | Sequence | K$_i$ Thrombin | K$_i$ Plasmin | K$_i$ Urokinase | K$_i$ tPA |
|---|---|---|---|---|---|
| 1c | 4-MeO-bs-Gly-Pro-4-Amba | 0.97 | 5,800 | 225,000 | 630 |
| 50 | 4-MeO-bs-Asn-Pro-4-Amba | 0.36 | 17,500 | 52,000 | 47,000 |
|  | 4-MeO-bs-Asn(PEG$_{2000}$-OMe)-Pro-4-Amba | 0.53 | 33,500 | 157,000 | 599,000 |

Interestingly, the K$_i$ values of the inhibitors listed in the table above show that the introduction of a suitable L-amino acid with a side chain not only results in an increase in the thrombin inhibition, but also diminishes the inhibition of the fibrinolytic enzymes plasmin and tPA. Accordingly, the compound comprising asparagine listed in the table and the PEG-coupled inhibitor are very effective and, at the same time, very selective thrombin inhibitors.

Example 9

Elimination of the Inhibitor Conjugates in Rats

Preliminary remarks: Female Wistar rats with a body weight between 150 to 250 g were used for the experiments. The animals were kept under conventional conditions and were provided with standard food and water ad libitum. Anaesthetization was carried out with 1.5 g ethylurethane per kg of body weight. Then the right and left jugular veins were prepared and catheters were inserted so that blood could be drawn at different points of time. The urine was collected throughout the entire test period and the inhibitor concentration was determined by means of a clotting test.

FIG. 5 shows the elimination of the compound of formula (IV) after intravenous administration of 10 mg/kg in a rat. The elimination half-life is about 16.5 min.

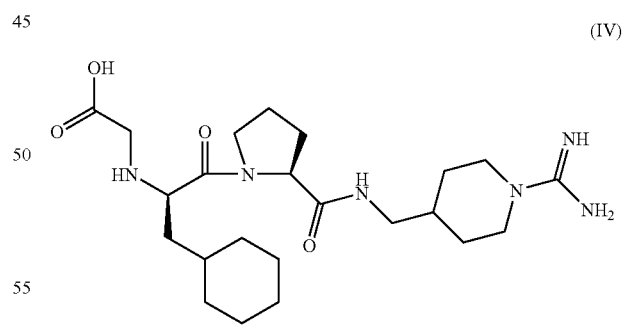

(IV)

FIG. 6 shows the results of the determination of the cumulative percentage recovery of the compound according to formula (IV) in the urine after subcutaneous administration to the rats. About 58% of the compound is recovered in the urine.

As a comparison, an example with an analogous compound is provided to which a PEG$_{5000}$ has been covalently coupled.

FIG. 7 shows the blood level of the compound according to formula (V) shown below (the PEG chain has an average molecular weight of 5,000 Da) after subcutaneous administration of 10 mg/kg. The elimination half-life was determined to be about 2.6 hours and is thus considerably longer compared to the free, non-PEG-coupled compound (cf. FIG. 5).

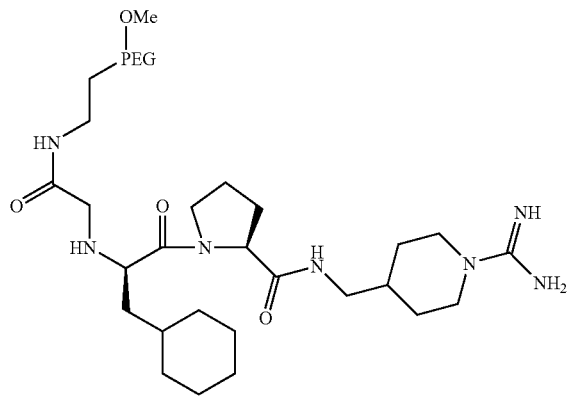

(V)

FIG. 8 shows the results of the determination of the cumulative percentage recovery of the compound according to formula (V) in the urine after subcutaneous administration to the rats (n=4). Almost 100% of the compound is recovered in the urine.

FIG. 9 shows a semilogarithmic plotting of the concentration-time curve after subcutaneous administration of 5 mg/kg of the inhibitor structure (VI) to rats. The elimination half-life was determined to be about 350 minutes. Thus, the half-life of this compound is clearly increased.

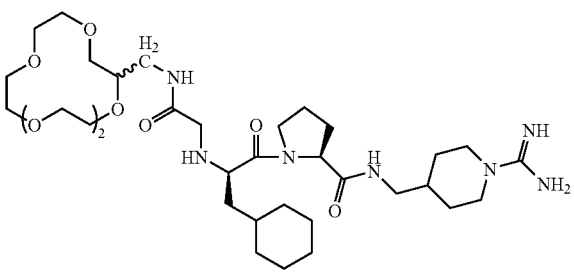

(VI)

Example 10

Elimination of the Inhibitor Conjugates in Pigs

Preliminary remarks: Female and male pigs with a body weight between 12 and 15 kg were used for the experiments. Anaesthetization was carried out with the intravenous administration of 20 mg/kg pentobarbital. A catheter for drawing blood was inserted into the left or right jugular vein, and a tracheal catheter was inserted into the windpipe to ensure good breathing of the animals during the tests. A catheter was also inserted into the bladder of the animals so that urine could be collected throughout the entire test period. In male pigs, the urethra was ligated in addition so that the urine could only flow from the bladder catheter into a collection vessel. The inhibitor concentrations were determined in the blood, the plasma and the urine by means of the Ecarin Clotting Test (Nowak and Bucha, (1996) Quantitative determination of hirudin in blood and body fluids. *Semin. Thromb.* 22, 197-202).

For the elimination tests in pigs, inhibitors of the general formula (VII) with an average PEG chain length of 2,000 or 10,000 Da were used.

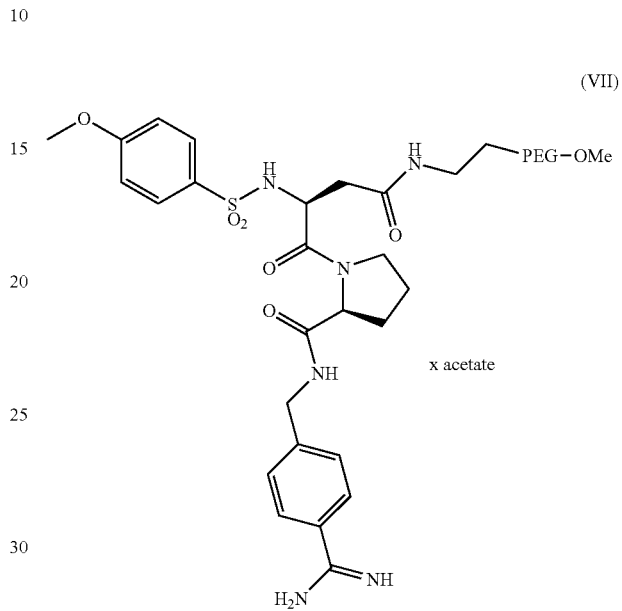

(VII)

The tests surprisingly showed that significant differences in the elimination rate of the inhibitors from the blood occurred depending on the length of the PEG chain in the inhibitors of formula (VII). In the case of inhibitors with an average PEG chain length of about 10,000 Da (FIGS. 12 and 13) prolonged blood levels with antithrombotic effect could be measured up to 28 hours after subcutaneous administration of the inhibitor. Interestingly enough, only 35% of the inhibitor was found in the urine until that point.

In contrast, the inhibitor of the general formula (VII) with an average PEG chain length of 2,000 Da is almost completely eliminated via the kidneys after about 12 hours (FIGS. 10 and 11).

Figure 1:
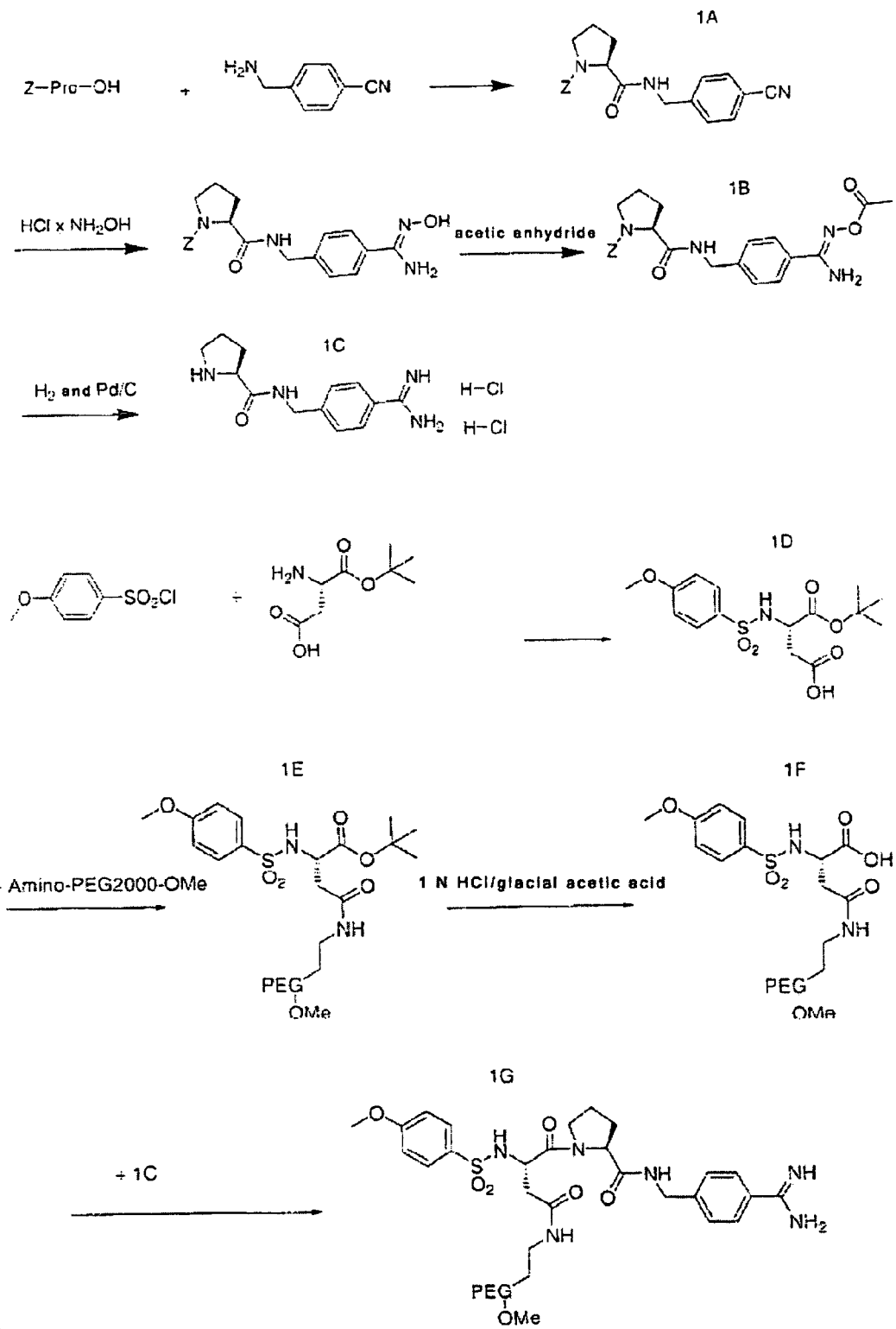
Figure 2:
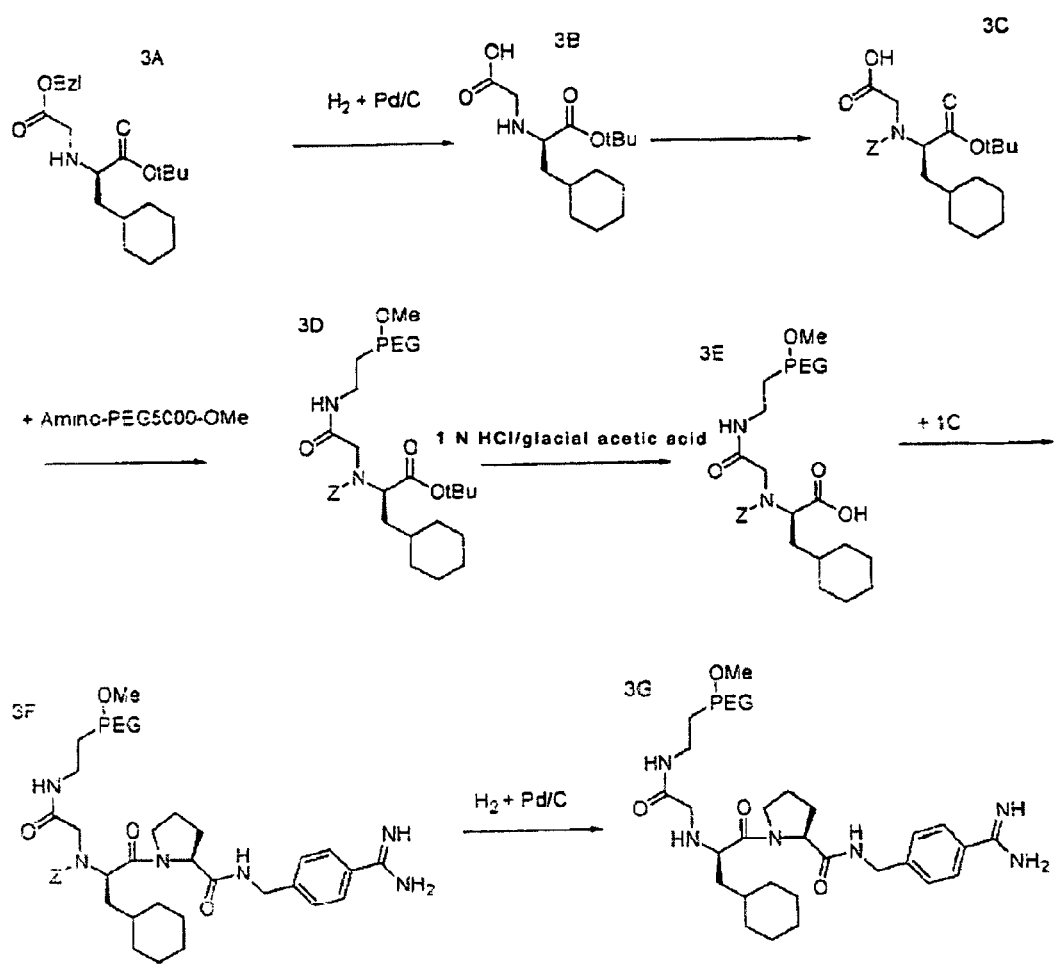
Figure 3:
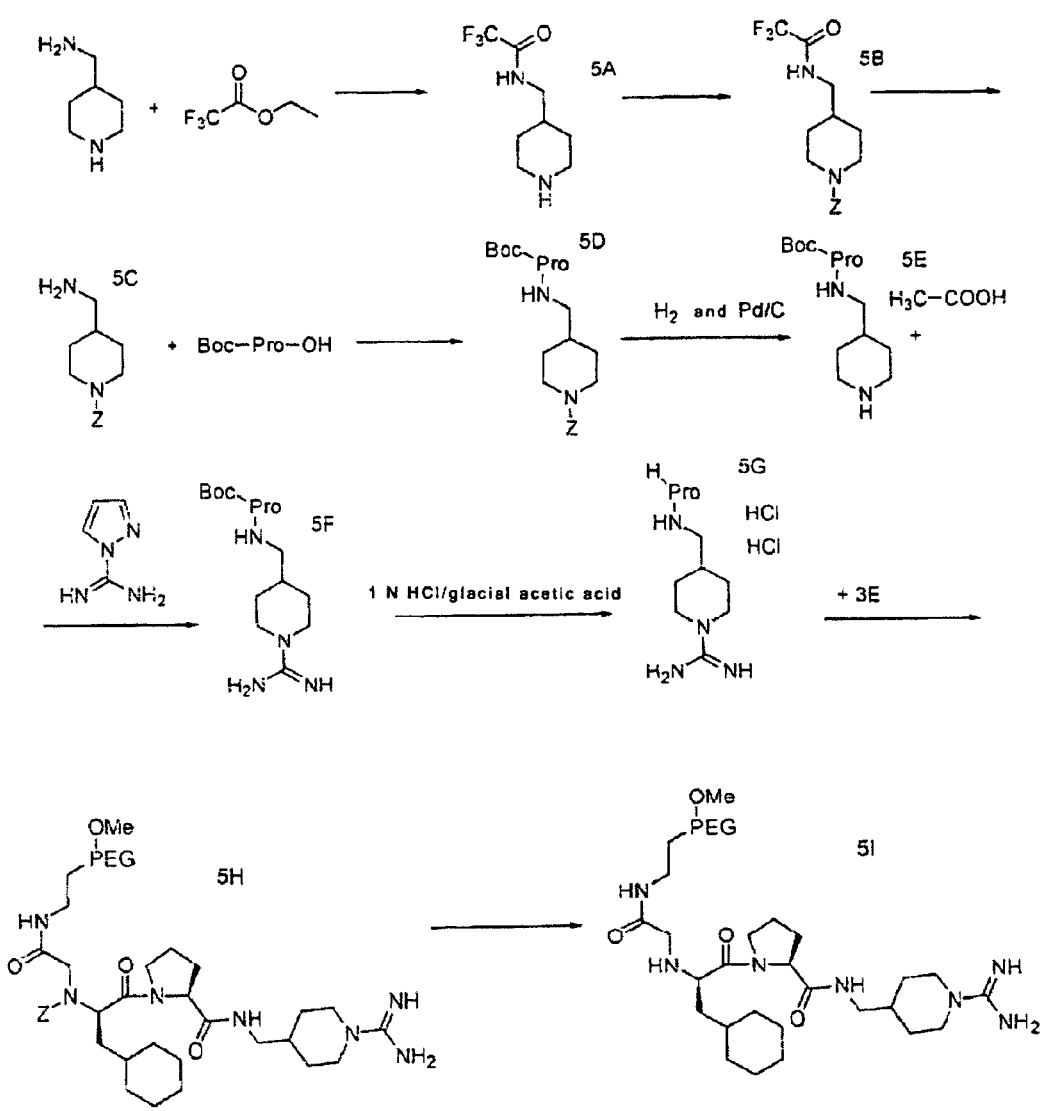
Figure 4:
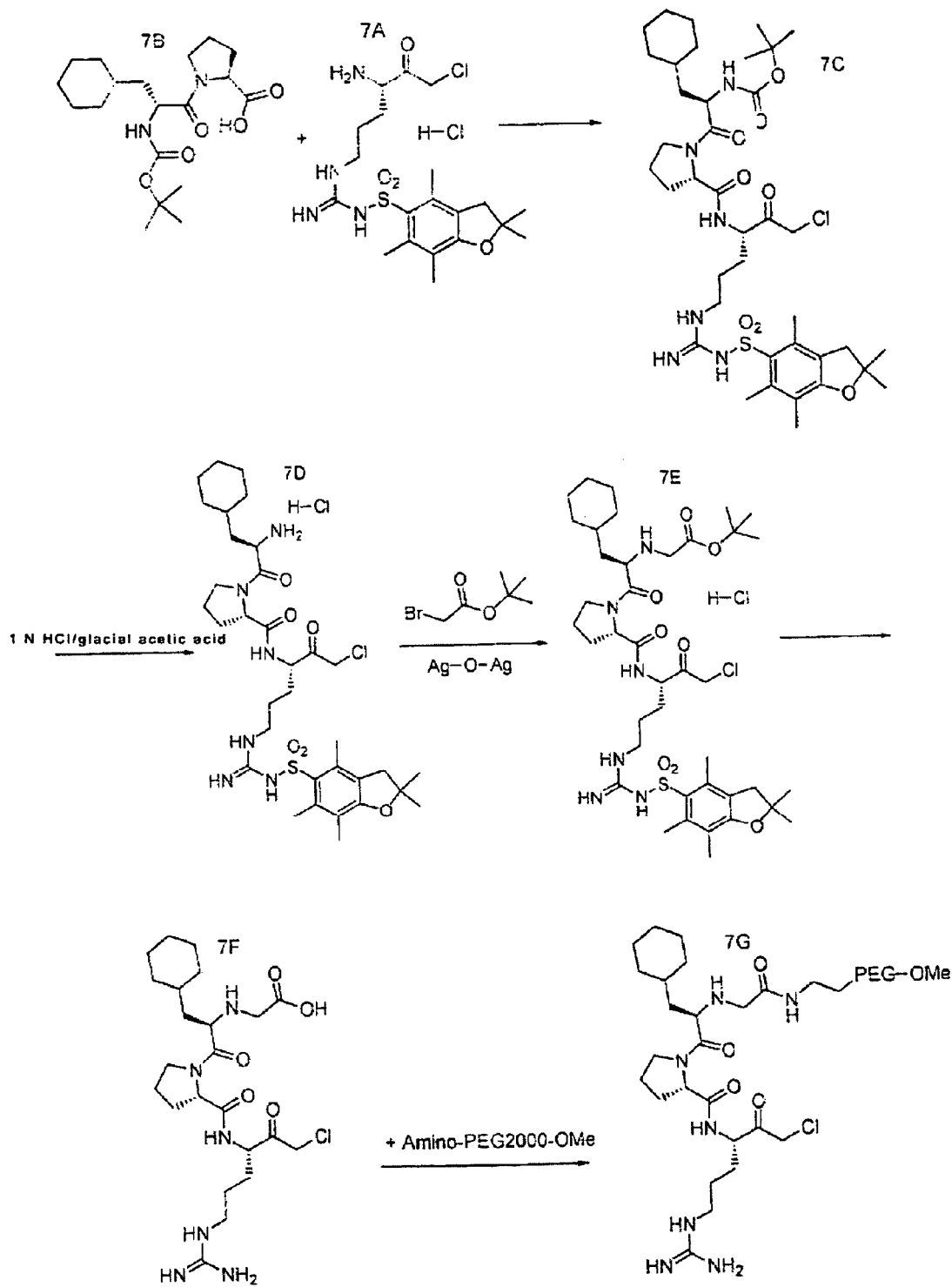
Figure 5:
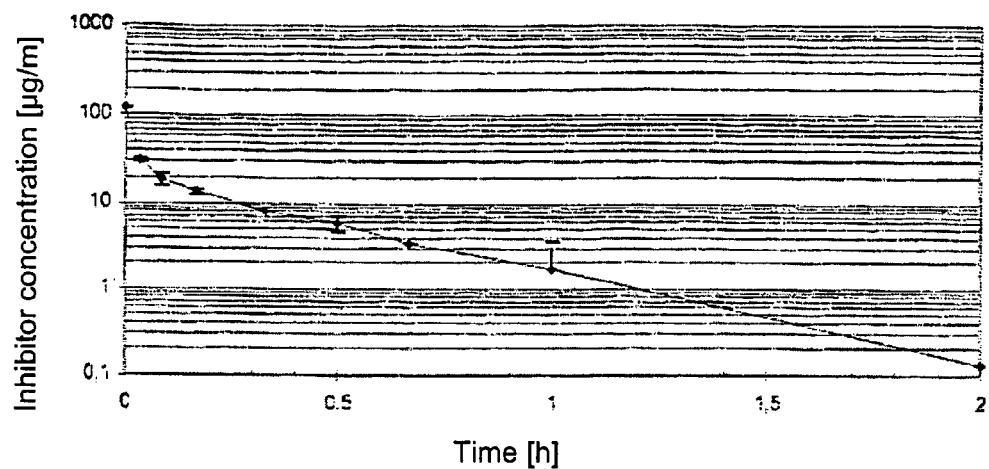
Figure 6:
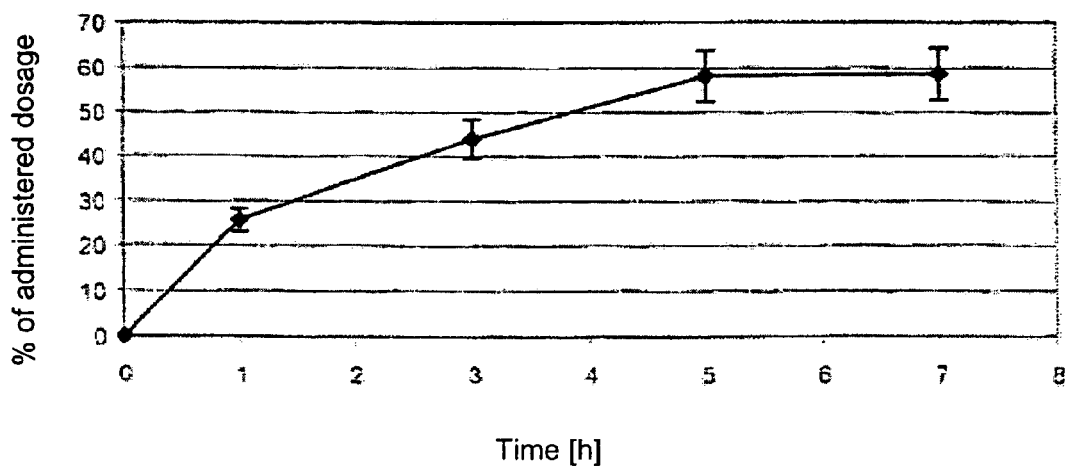
Figure 7:
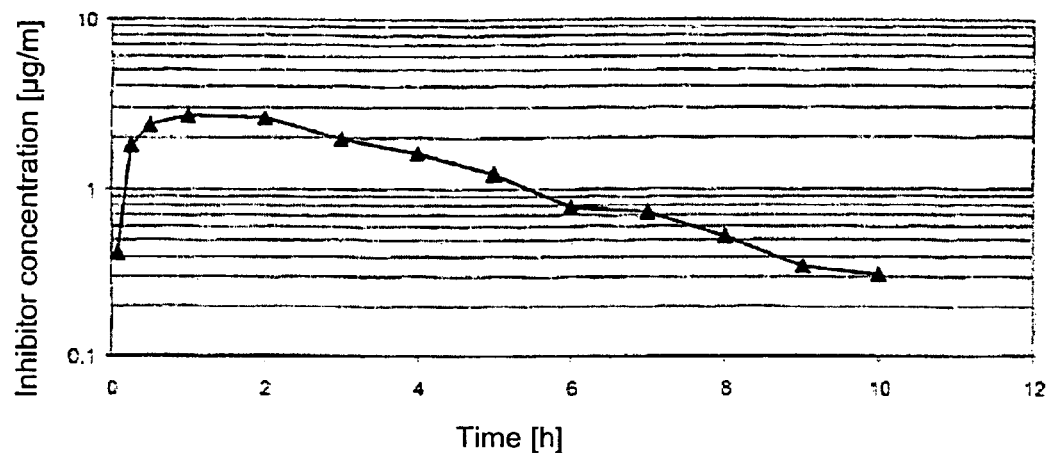
Figure 8:
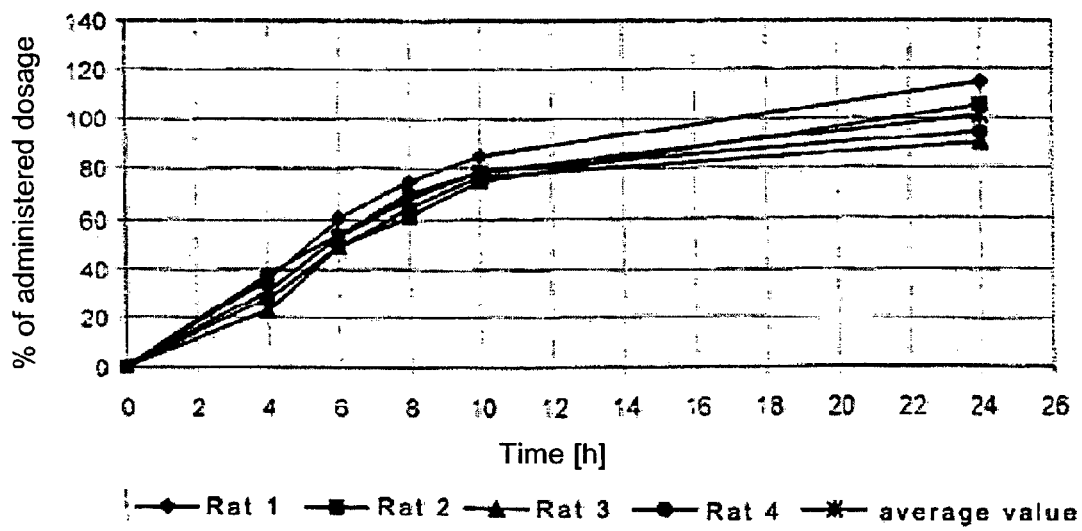
Figure 9:
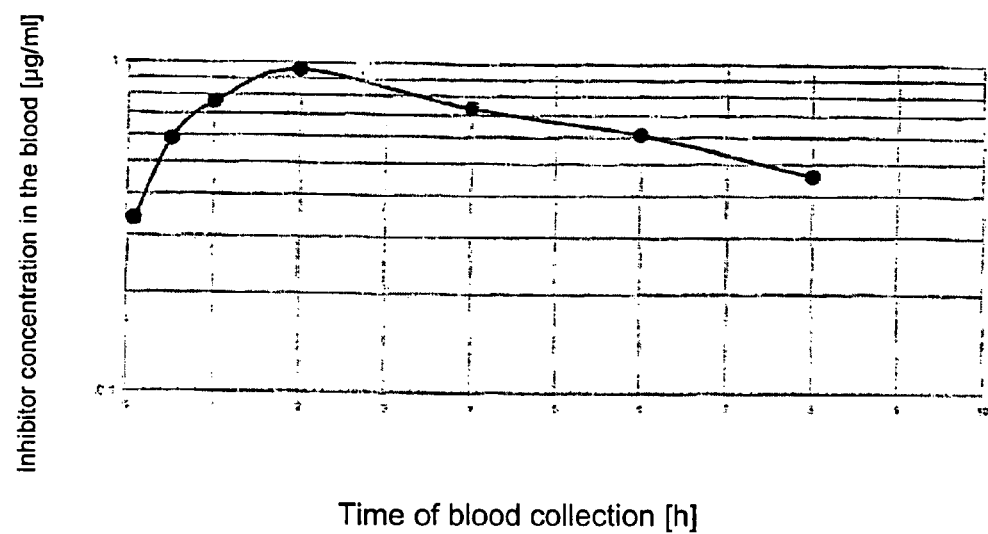
Figure 10:
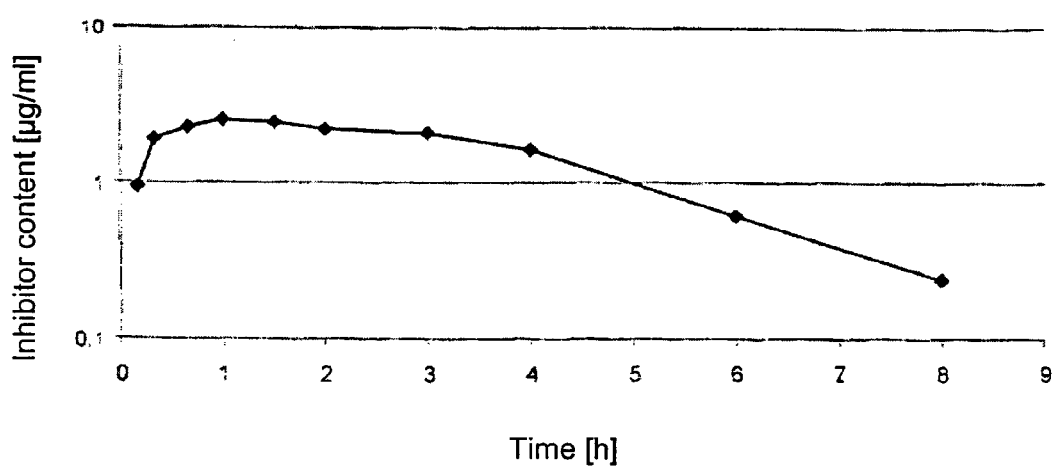
FIG. 10 shows the plasma levels of the inhibitor of the general structure (VII) with an average PEG chain of about 2,000 Da after subcutaneous administration of 2.5 mg/kg in pigs.
Figure 11:
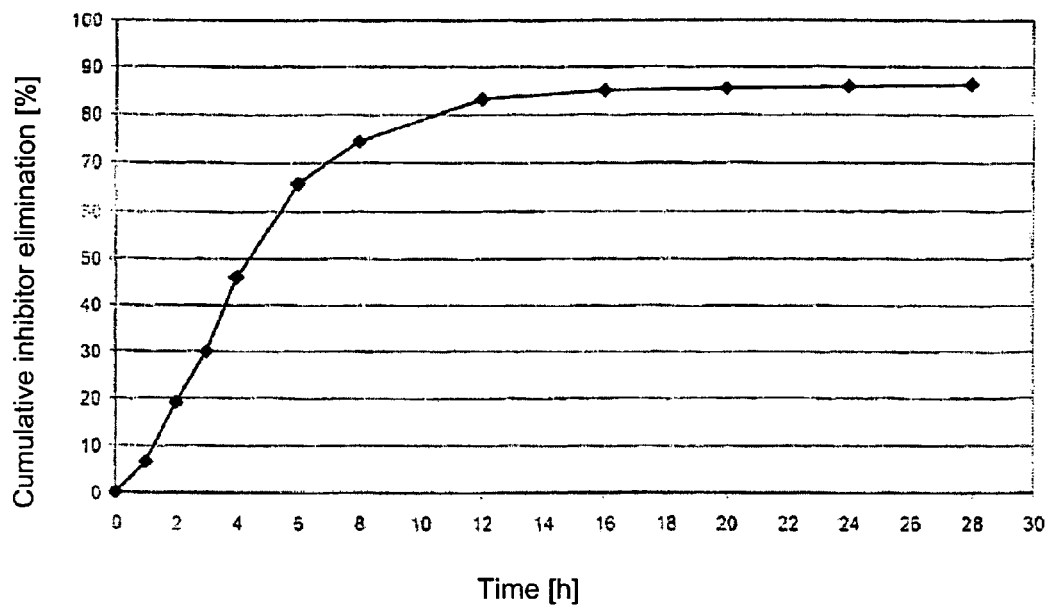
FIG. 11 shows the cumulative elimination of the inhibitor of the general structure (VII) with an average PEG chain of about 2,000 Da after subcutaneous administration of 2.5 mg/kg in the urine of pigs.
Figure 12:
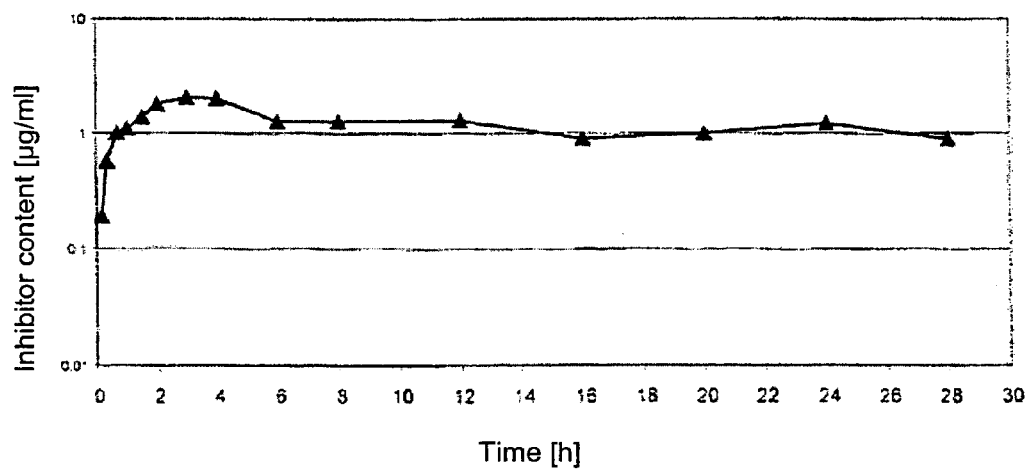
FIG. 12 shows the plasma levels of the inhibitor of the general structure (VII) with an average PEG chain of about 10,000 Da after subcutaneous administration of 20 mg/kg in pigs.
Figure 13:
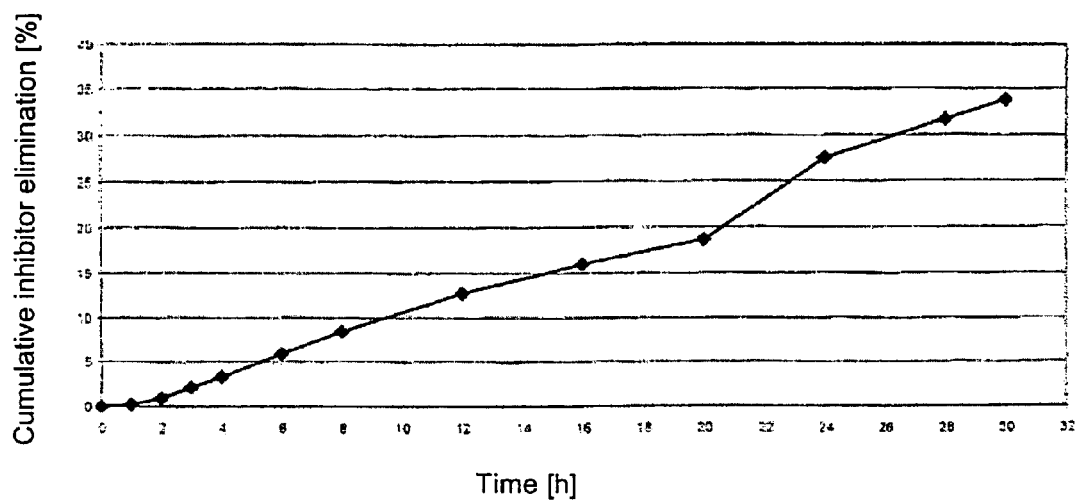
FIG. 13 shows the cumulative elimination of the inhibitor of the general structure (VII) with an average PEG chain of about 10,000 Da after subcutaneous administration of 20 mg/kg in the urine of pigs.

The invention claimed is:

1. Compound of the general structure (I)

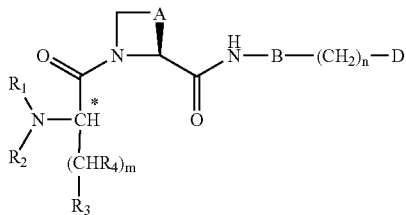

wherein m is 0, 1, 2, 3 or 4;

n is 0, 1, 2, 3, 4 or 5;

A is either a methylene, ethylene or propylene group and the ring formed therewith can be unsubstituted or substituted with a hydroxyl group, which is optionally etherified with an alkyl or aralkyl, or one of the groups —CH$_2$—O—, —CH$_2$—S—, —CH$_2$—SO—, —CH$_2$—O—CH$_2$—, —CH$_2$—S—CH$_2$—, —CH$_2$—SO—CH$_2$—;

B is a bond or

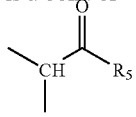

wherein R$_5$ is alkyl comprising 1 to 4, preferably 1 or 2 and especially preferred one carbon atom, and can be substituted with one or more identical or different halogen atoms or with a group

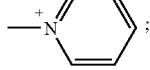

D represents a group

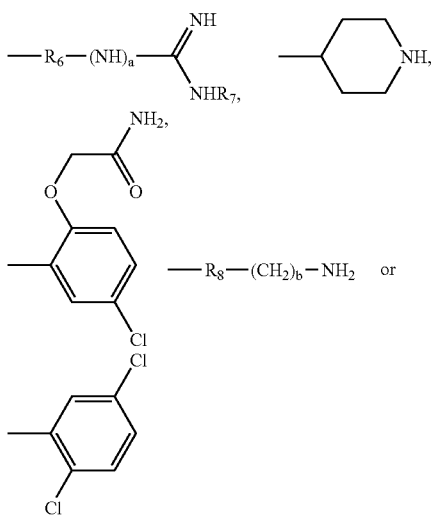

wherein a is 0 or 1, b is 0, 1 or 2, and R$_6$ and R$_8$ are independently bivalent groups selected from aromatic or saturated 6-membered rings which can comprise a heteroatom in addition to carbon and can carry one or more identical or different alkyl substituents, and wherein R$_6$ can furthermore be —NH— if a is 0, and R$_7$ is a hydrogen atom or —NH$_2$;

R$_1$ is a hydrogen atom or arylsulfonyl, aralkylsulfonyl, cycloalkylmethylsulfonyl, cyclo-alkylethylsulfonyl or alkylsulfonyl group, the aryl portion of which can optionally carry one, two, three, four or five substituents independently selected from halogen atoms, alkyl or alkoxy groups or is linked with another aryl, and either:

R$_2$ is —(CH$_2$)$_p$—CO—NH—(CH$_2$)$_q$—X, —(CH$_2$)$_r$—NH—CO—(CH$_2$)$_s$—V—X or —(CH$_2$)$_r$—NH—CO—O—(CH$_2$)$_s$—V—X wherein p is an integer from 1 to 5 and q is an integer from 2 to 5;

r is an integer from 2 to 5 and s is an integer from 1 to 5;

V is a bond or —CO—NH—(CH$_2$)$_c$— and c is an integer from 2 to 5; and

X is an oligo or polyalkylene glycol with the structure —[O—(CH$_2$)$_d$]$_e$—OZ or —[O—CH(CH$_3$)—CH$_2$]$_e$—OZ or a cycle with the structure

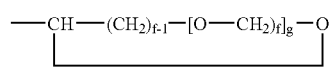

and d is an integer from 2 to 6, e is an integer from 3 to 1,000, Z is a hydrogen atom or alkyl or replicates the entire inhibitor structure bonded to the free valence of the group X, f is an integer from 2 to 6 and g is an integer from 3 to 10; and R$_3$ is a phenyl or cyclohexyl group which can be substituted with 1 to 5 identical or different substituents independently selected from halogen atoms, alkyl, alkoxy or hydroxyl groups and R$_4$ is a hydrogen atom, phenyl or cyclohexyl group which can be substituted with 1 to 5 identical or different substituents independently selected from halogen atoms, alkyl, alkoxy or hydroxyl groups, m is 0, 1, 2, 3 or 4 and a D-configuration is present at the carbon atom marked with *;

or

R$_2$ is a hydrogen atom and

R$_3$ is —CO—NH—(CH$_2$)$_q$—X, —CO—W$_1$—W$_2$—(CH$_2$)$_q$—X, —NH—CO—(CH$_2$)$_s$—V—X, —NH—CO—O—(CH$_2$)$_s$—V—X, —S—CH$_2$—CO—NH—(CH$_2$)$_t$—X or —S—S—CH$_2$—CH$_2$—X, wherein q, s, X and V are as defined above and t is an integer from 2 to 5, and the group W$_1$ is —O— or —NH— and W$_2$ represents a bond or has the structure —(CH$_2$)$_v$—Ph—(CH$_2$)$_{v'}$-amide-, wherein v and v' are independently 0, 1 or 2, Ph represents a 1,2-, 1,3- or 1,4-substituted phenyl and amide represents —HN—(O)C— or —C(O)NH—, and R$_4$ is a hydrogen atom, m is 1, 2, 3, 4 or 5 and an L-configuration is present at the carbon atom marked with *.

2. Compound according to claim 1, wherein B represents one of the following structures

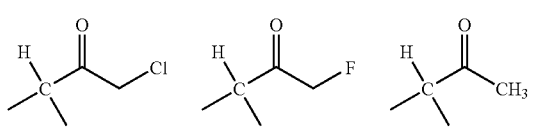
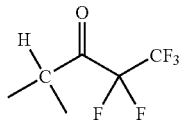
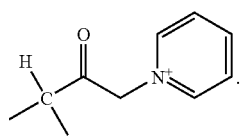
3. Compound according to claim 1, wherein D represents one of the following structures
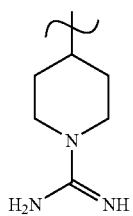
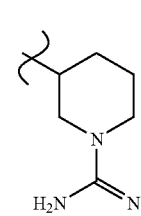
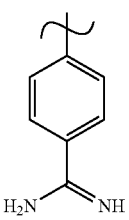
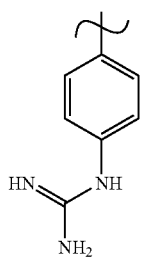
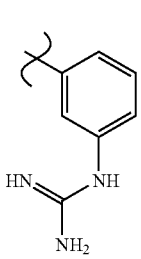
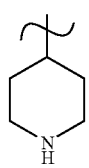
-continued
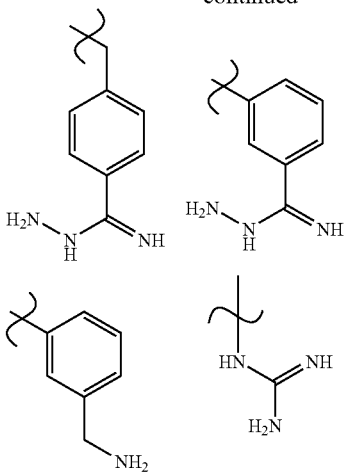
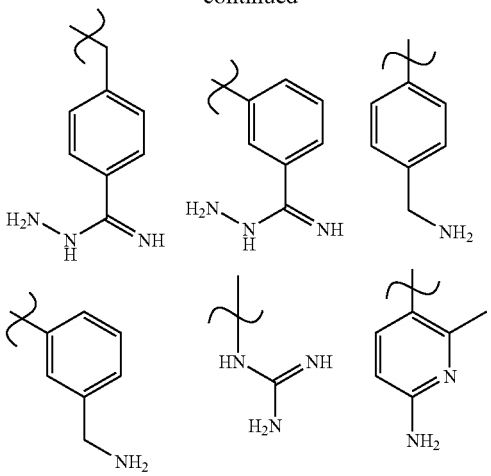
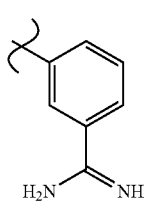
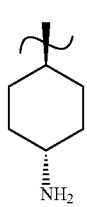
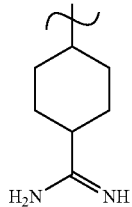
4. Compound according to claim 1, wherein X has a cyclic structure of the formula
$$—CH—(CH_2)_{f-1}—[O—CH_2)_f]_g—O—$$
and f and g are as defined in claim 1.
5. Compound according to claim 1 having one of the following formulas Ia to Ih
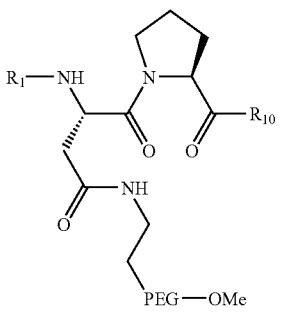
(Ia)

(Ib)
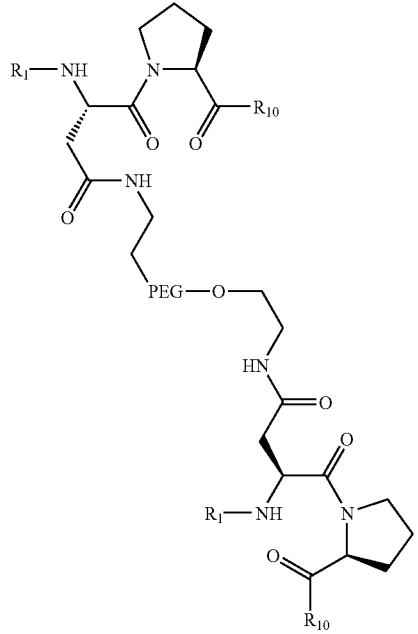
(Ic)
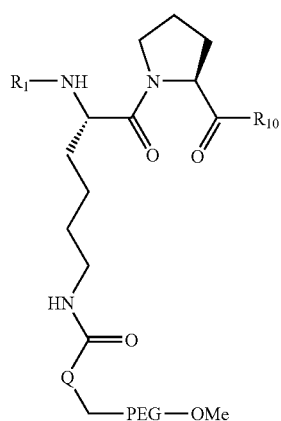
(Id)
(Ie)
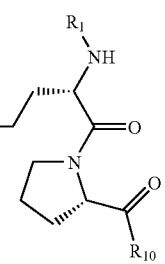
(If)
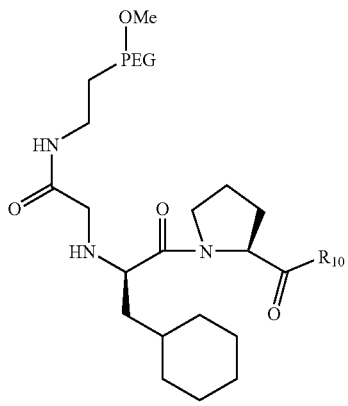

-continued
(Ig)
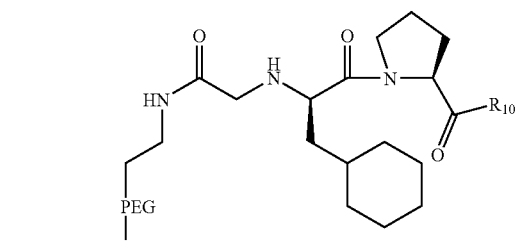
(Ih)
wherein $R_1$ is a 4-methoxy-phenylsulfonyl, 4-methoxy-3-chloro-phenylsulfonyl, 4-methoxy-3-methyl-phenylsulfonyl or 4-methoxy-2,3,6-trimethyl-phenylsulfonyl group,
Q is —(CH$_2$)s'—, wherein s'=0, 1, 2, 3 or 4, —O—CH$_2$— or —CH$_2$—CH$_2$—CO—NH—CH$_2$,
and
PEG is a polyethylene glycol structure of the formula —[O—C$_2$H$_4$]$_i$—, wherein i is 3 to 1,000, h represents 1, 2, 3 or 4
and $R_{10}$ is
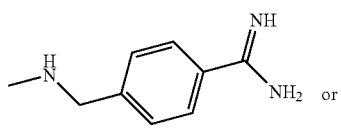 or
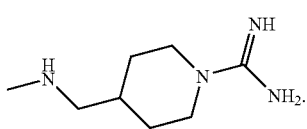.
* * * * *